(12) United States Patent
Kim et al.

(10) Patent No.: US 12,258,556 B2
(45) Date of Patent: Mar. 25, 2025

(54) INTEGRATED SYRINGE

(71) Applicant: UNIVERSITY OF CENTRAL FLORIDA RESEARCH FOUNDATION, INC., Orlando, FL (US)

(72) Inventors: Brian Kim, Orlando, FL (US); Geoffrey Mulberry, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 714 days.

(21) Appl. No.: 17/622,968

(22) PCT Filed: Jun. 26, 2020

(86) PCT No.: PCT/US2020/039798
§ 371 (c)(1),
(2) Date: Dec. 27, 2021

(87) PCT Pub. No.: WO2020/264277
PCT Pub. Date: Dec. 30, 2020

(65) Prior Publication Data
US 2022/0267757 A1    Aug. 25, 2022

Related U.S. Application Data

(60) Provisional application No. 62/867,038, filed on Jun. 26, 2019.

(51) Int. Cl.
*G01N 1/00* (2006.01)
*B01L 3/00* (2006.01)
(Continued)

(52) U.S. Cl.
CPC .... *C12N 15/1017* (2013.01); *B01L 3/502753* (2013.01); *C12Q 1/701* (2013.01);
(Continued)

(58) Field of Classification Search
None
See application file for complete search history.

(56) References Cited

U.S. PATENT DOCUMENTS 3,572,336 A     3/1971   Hershberg
11,207,689 B2 * 12/2021  Cho .................... C12N 15/1003
(Continued)

FOREIGN PATENT DOCUMENTS

EP          2514455 A1    4/2011

OTHER PUBLICATIONS

Ali, Nasir et al., "Current Nucleic Acid Extraction Methods and Their Implications to Point-of-Care Diagnostics", BioMed Research International, 2017, vol. 2017, Article ID 9306564, 13 pages.
(Continued)

*Primary Examiner* — Jyoti Nagpaul
(74) *Attorney, Agent, or Firm* — Timothy H. Van Dyke; Wolter Van Dyke Davis, PLLC

(57) ABSTRACT

Various embodiments relate to a syringe for separating nucleic acids from a blood sample and systems that include the syringe and a portable PCR device. The syringe may include a shell defining a central aperture extending through a longitudinal axis of the syringe, a plunger disposed within the central aperture of the shell, and a core rotatably disposed within the central aperture. The syringe may further include a needle fluidically connectable to the inlet of the shell. Various embodiments relate to a method for separating nucleic acids from a blood sample, the method comprising drawing the blood sample from a patient using the syringe according to any of the embodiments described herein.

11 Claims, 24 Drawing Sheets

(51) Int. Cl.
    *C12N 15/10*     (2006.01)
    *C12Q 1/70*     (2006.01)

(52) U.S. Cl.
    CPC ... *B01L 2200/16* (2013.01); *B01L 2300/0681* (2013.01); *B01L 2300/0832* (2013.01); *B01L 2400/0487* (2013.01); *B01L 2400/06* (2013.01); *C12Q 2600/112* (2013.01)

(56) References Cited

U.S. PATENT DOCUMENTS

| | | |
|---|---|---|
| 2002/0182718 A1 | 12/2002 | Malmquist |
| 2006/0203608 A1 | 9/2006 | Barker et al. |
| 2009/0043282 A1 | 2/2009 | Hughes et al. |
| 2011/0224642 A1 | 9/2011 | Fojtik |
| 2012/0016313 A1 | 1/2012 | Nalesso et al. |
| 2014/0018729 A1 | 1/2014 | Foster et al. |
| 2014/0350460 A1 | 11/2014 | Moore |
| 2014/0358091 A1 | 12/2014 | Johannesson et al. |
| 2014/0364831 A1 | 12/2014 | Ciancarelli |
| 2015/0025454 A1 | 1/2015 | Wetzel et al. |
| 2017/0281141 A1 | 10/2017 | Lampropoulos et al. |

OTHER PUBLICATIONS

Almassian, David R. et al., "Portable nucleic acid thermocyclers", Chem. Soc. Rev., 2013, vol. 42, pp. 8769-8798.
Bell, David, "Letter to the Editor Malaria Rapid Diagnostic Tests: One Size May Not Fit All", Clinical Microbiology Reviews, Oct. 2002, vol. 15, No. 4, pp. 771-772.
Boom, R. et al., "Rapid and Simple Method for purification of Nucleic Acids", Journal of Clinical Microbiology, Mar. 1990, vol. 28, pp. 495-503.
Carod-Artal, Francisco Javier, "Neurological complications of Zika virus infection", Expert Review of Anti-infective Therapy, 2018, vol. 16, No. 5, pp. 399-410.
CDC, "Guidance for U.S. Laboratories Testing for Zika Virus Infection", Jul. 26, 2016, 12 pages.
Chin, Curtis D. et al., "Chapter 1 Low-Cost Microdevices for Point-of-Care Testing", Point-of-Care Diagnostics on a Chip, 2013, 20 pages.
Cugola, Fernanda R. et al., "The Brazilian Zika virus strain causes birth defects in experimental models", Nature, Nov. 11, 2016, vol. 534, No. 7606, pp. 267-271.
Engel, Nora et al., "Addressing the challenges of diagnostic demand and supply: insights from the online global health discussion platform", BMJ Global Health, 2016, vol. 1, 8 pages.
Hanscheid, Thomas et al., "Point-of-care tests: where is the point?", The Lancet, Oct. 2014, vol. 14, p. 922.
Ho, Nga T., Sample Concentration and Purification for Point-of-Care Diagnostics, Conf Proc IEEE Eng Med Biol Soc., 2012, vol. 2012, pp. 2396-2399.
Honein, Margaret A. et al., "Birth Defects Among Fetuses and Infants of USWomen With Evidence ofPossible ZikaVirus InfectionDuringPregnancy", JAMA. 2017, vol. 317.
Johnston, Stephanie P. et al., "PCR as Confirmatory Technique for Laboratory Diagnosis of Malaria", Journal of Clinical Microbiology, Mar. 2006, vol. 44, No. 3, pp. 1087-1089.
Koo, Chiwan et al., "Development of a Real-Time Microchip PCR System for Portable Plant Disease Diagnosis", PLOS One, 2013, vol. 8, issue 12, 11 pages.
Kozel, Thomas R. et al., "Point-of-Care Testing for Infectious Diseases: Past, Present, and Future", J Clin Microbiol, Aug. 2017, vol. 55, issue 8, pp. 2313-2320.
Mabey, David et al., "Rapid and simple point of care diagnostics for STIs", Sex Transm Inf. 2001, vol. 77, pp. 397-401.
Mabey, David et a., "Diagnostics for the developing world", Nature Reveiws Microbiology, Mar. 2004, vol. 2, pp. 231-240.
Marshall, R. et al., "Characteristics of the m2000 Automated Sample Preparation and Multiplex Real-Time PCR System for Detection of Chlamydia trachomatis and Neisseria gonorrhoeae", Journal of Clinical Microbiology, Mar. 2007, vol. 45, No. 3, pp. 747-751.
Moody, Anthony, "Rapid Diagnostic Test for Malaria Parasites", Clinical Microbiology Reviews, Jan. 2022, vol. 15, No. 1, pp. 66-78.
Mulberry, Geoffrey et al., "Handheld Battery-operated Sample Preparation Device for qPCR Nucleic Acid Detections using Simple Contactless Pouring", Analytical Methods, 2018, pp. 1-3.
Mulberry, Geoffrey et al., "3D printing andmilling a real-time PCR device for infectious disease diagnostics", PLoS One, 2017, vol. 12, No. 6, 18 pages.
Mulberry, Geoffrey et al., "Handheld Battery-operated Sample Preparation Device for qPCR Nucleic Acid Detections using Simple Contactless Pouring", Analytical Methods, 2018, pp. 1-9.
Noordhoek, Gerda T. et al., "Reliability of Nucleic Acid Amplification for Detection of *Mycobacterium tuberculosis*: an International Collaborative Quality Control Study among 30 Laboratories", Journal of Clinical Microbiology, Oct. 1996, vol. 34, No. 10, pp. 2522-2525.
Ochodo, Eleanor et al., "Achieving universal testing for malaria", BMJ, 2016, vol. 352, 6 pages.
Pang, Junxiong et al., "Progress and Challenges towards Point-of-Care Diagnostic Development for Dengue", Journal of Clinical Microbiolog, Dec. 2017, vol. 55, issue 12, pp. 3339-3349.
Parra, Beatriz et al., "Guillain-Barré Syndrome Associated with Zika Virus Infection in Colombia", N Engl J Med, Oct. 20, 2016, vol. 375, No. 16, pp. 1513-1523.
Poh, Jun-Jie et al., "Comparison of customized spin-column and salt-precipitation finger-prick blood DNA extraction", Biosci. Rep, 2014, vol. 34, pp. 629-634.
Price, Christopher P., "Point of care testing", BMJ, May 26, 2001, vol. 322, pp. 1285-1288.
Rasmussen, Sonja A. et al., "Zika Virus and Birth Defects—Reviewing the Evidence for Causality", The new engl and journal o f medicine, May 19, 2016, vol. 374, No. 20, pp. 1981-1987.
Reyburn, Hugh, "New WHO guidelines for the treatment of malaria", BMJ, 2010, vol. 340, 4 pages.
Rosenberg, Nora E. et al., "Detection of Acute HIV Infection: A Field Evaluation of the Determine HIV-1/2 Ag/Ab Combo Test", The Journal of Infectious Diseases, 2012, vol. 205, pp. 528-534.
Sher, Mazhar et al., "Paper-based analytical devices for clinical diagnosis: recent advances in the fabrication techniques and sensing mechanisms", Expert Rev Mol Diagn. Apr. 2017, vol. 17, No. 4, pp. 351-366.
Sia, Samual K. et al., "Microfluidics and point-of-care testing", Lab on Chip, The Royal Society of Chemistry, 2008, 5 pages.
Silva, Ivan Rocha Ferreira da et al., "Neurologic Complications Associated with the Zika Virus in Brazilian Adults", Jama Neurol., Oct. 2017, vol. 74, No. 10, pp. 1190-1198.
Snoeblen, Kathleen F., "Engineering Professor Advancing Brain-Machine Interface and Medical Diagnostic Technologies", htpps://www.ece.ucf.edu/~bkim/index.php, Nov. 2019, 3 pages.
Stauffer, William M. et al., "Diagnostic Performance of Rapid Diagnostic Tests versus Blood Smears for Malaria in US Clinical Practice", Clinical Infectious Diseases, 2009, vol. 49, pp. 408-413.
St John, Andrew et al., "Existing and Emerging Technologies for Point-of-Care Testing", Clin Biochem Rev, 2014, vol. 35, No. 3, pp. 155-167.
Valentine-Thon, Elizabeth, Quality control in nucleic acid testing—where do we stand?, Journal of Clinical Virology, 2002, vol. 25, pp. s13-s21.
Waggoner, Jesse J. et al., "Single-Reaction Multiplex Reverse Transcription PCR for Detection of Zika, Chikungunya, and Dengue Viruses", Emerging Infectious Diseases, Jul. 2016, vol. 22, No. 7, pp. 1295-1297.
Weaver, Scott C. et al., "Chikungunya Virus and the Global Spread of a Mosquito-Borne Disease", N Engl J Med, 2015, pp. 1231-1239.
WHO, "Recommended selection criteria for procurement of malaria rapid diagnostic tests", Global Malaria Programme, Mar. 2016, 16 pages.
WHO, "Dengue Guidelines for Diagnosis, Treatment, Prevention and Control", World Health Organization, 2009, 160 pages.

(56) References Cited

OTHER PUBLICATIONS

WHO, "Zika and Potential Complications", Zika Situation Report, Feb. 12, 2016, 6 pages.
Wongsrichanalai, Chansuda et al., "A Review of Malaria Diagnostic Tools: Microscopy and Rapid Diagnostic Test (RDT)", Am. J. Trop. Med. Hyg., 2007, vol. 77, Suppl 6, pp. 119-127.
Yadava, Preeti et al., "Effect of Lyophilization and Freeze-thawing on the Stability of siRNA-liposome Complexes", AAPS PharmSciTech, Jun. 2008, vol. 9, No. 2, pp. 335-341.

* cited by examiner

Direction of Flow

FIG. 20A
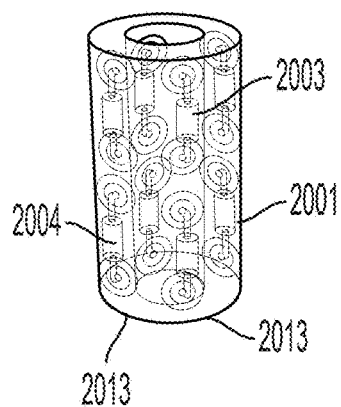
FIG. 20B
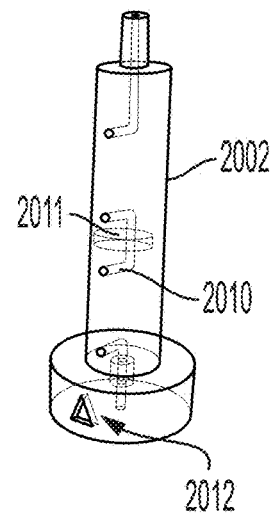
FIG. 20C
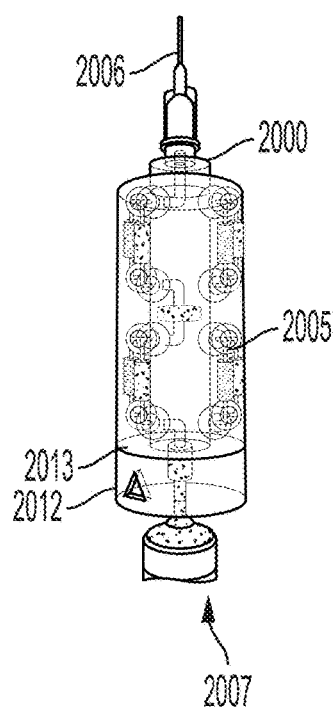
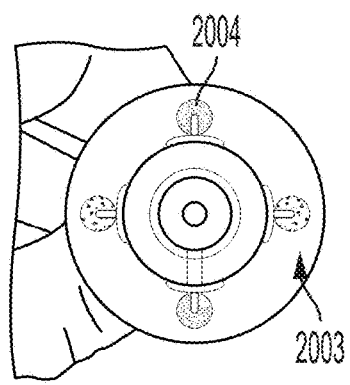
FIG. 20D
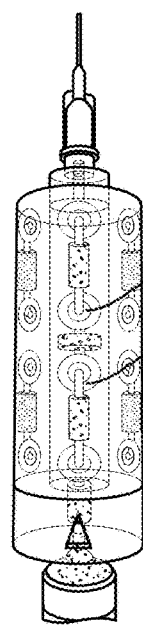
FIG. 20E
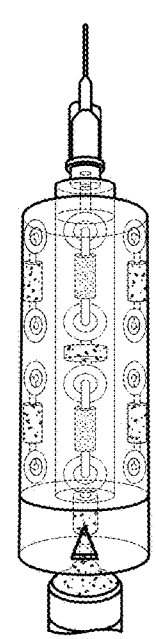
FIG. 20F
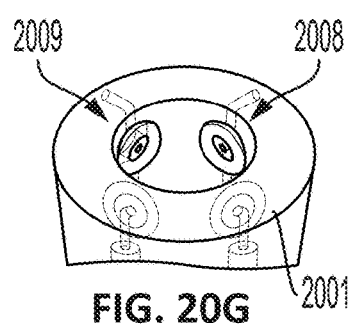
FIG. 20G

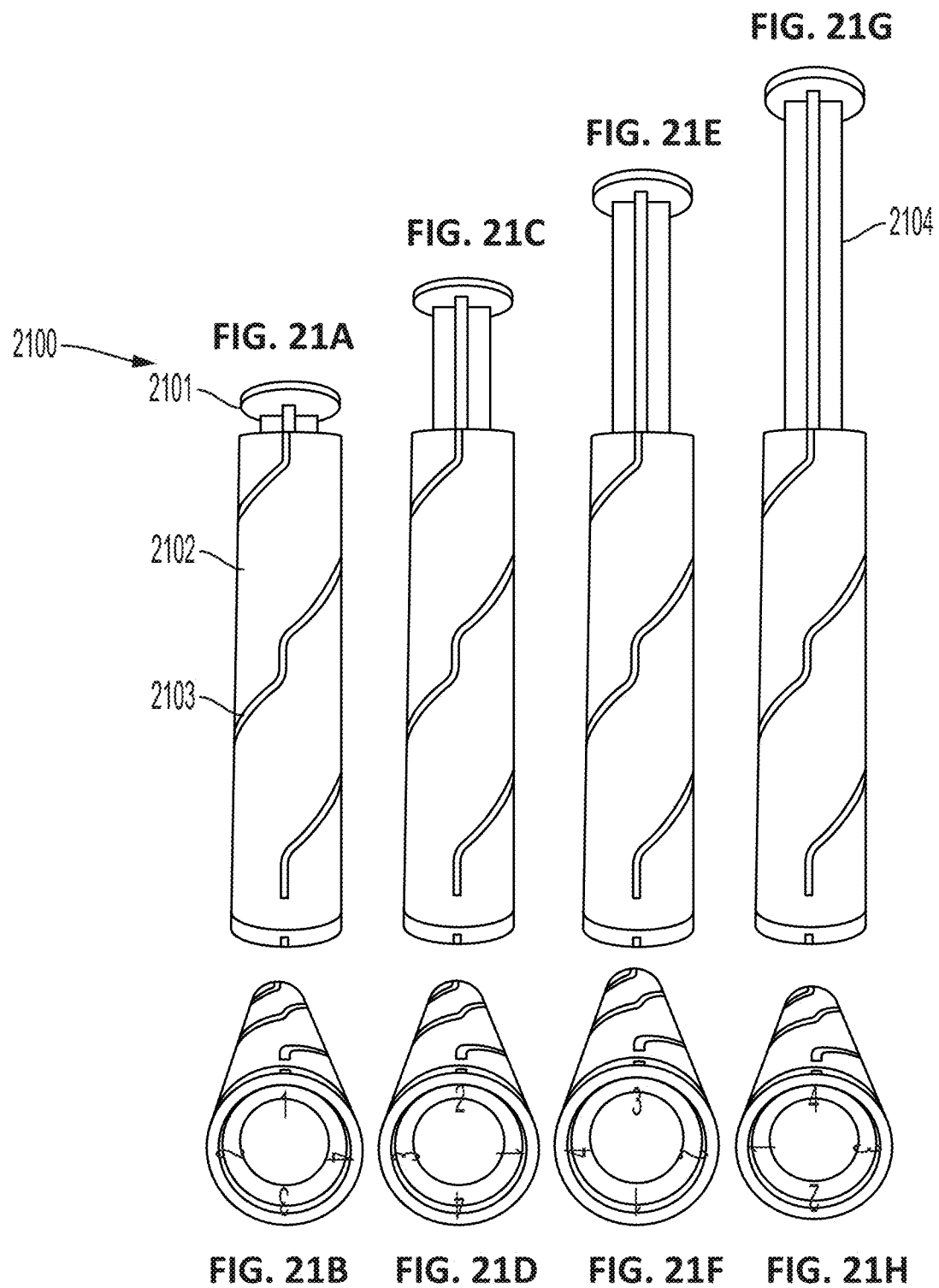

INTEGRATED SYRINGE

CROSS-REFERENCE TO RELATED APPLICATION

This application claims the benefit of U.S. Provisional Patent Application No. 62/867,038, filed Jun. 26, 2019, titled SAMPLE COLLECT-PURIFY INTEGRATED SYRINGE, which is incorporated by reference herein in its entirety.

BACKGROUND

The discussion of shortcomings and needs existing in the field prior to the present invention is in no way an admission that such shortcomings and needs were recognized by those skilled in the art prior to the present disclosure.

Mosquito-borne diseases such as Zika, dengue, and chikungunya viruses impose threats to many populations worldwide, including the United States, with nearly 1.5 million cases of Zika virus infection since 2015 and nearly 5,000 cases reported in the United States since 2016, which can cause severe birth defects and other neurological complications, and 50-100 million dengue virus infections yearly with 22,000 deaths. Diagnosing mosquito-borne diseases in the early stage is crucial in limiting the spread among the population (through bites of infected mosquitos and sexual transmission) as well as preventing serious illness to the patient. Many early-stage diagnostic devices have been developed in recent years to detect pathogens with improved sensitivity and simpler/cheaper devices, but they fail to improve the medical logistical system for early diagnostics of infectious diseases, due to the labor-intensive sample preparation process.

Current methods result in long delays in diagnosis due to the sample preparation process. Sample preparation is a process that is involved in every diagnostic biochemical assay using whole blood. In this process, target molecules such as nucleic acids and proteins are extracted and purified from whole blood by removing other components of blood which can impede the detection mechanism. Currently, when a person experiences illness and is speculated to have been infected with common pathogens, the patient's blood is drawn and transported to a centralized laboratory where the sample preparation and detection take place. Depending on the location, transportation can take hours to days. Long transportation times can cause delay in diagnosis and may also result in sample degradation. Sample degradation may result in an inaccurate diagnosis at a centralized laboratory. At the laboratory, the blood undergoes sample preparation steps, which involve blood lysis, DNA/RNA capture, washing, and elution. The current sample preparation method can only be done by a skilled person and is conducted in a specialized laboratory. Despite such limitations, this procedure has minimally changed over the last two decades.

According to the Centers for Disease Control and Prevention (CDC), for diseases such as the Zika virus (ZIKV), dengue virus (DENV), and chikungunya virus (CHIKV), Real-Time Reverse Transcription-Polymerase Chain Reaction (rRT-PCR) is highly recommended to obtain a diagnosis and to determine the proper treatment, because rRT-PCR reveals both the quantity and the presence of the pathogen with high sensitivity and specificity. However, the real-time PCR machine, which operates rRT-PCR, has been prohibitively expensive (>$30,000) for small clinics and medical operations, and is only located in a centralized laboratory. Therefore, alternative techniques with a more accessible nature, such as rapid diagnostic tests (RDT), are often used to make a diagnosis at the cost of inaccuracy.

An urgent need exists for simple, low-cost, robust sample collection and sample processing tools requiring no power or skilled labor to enable early diagnosis of infectious disease.

BRIEF SUMMARY

Various embodiments relate to a syringe for separating nucleic acids from a blood sample. The syringe may include a shell defining a central aperture extending through a longitudinal axis of the syringe, a plunger disposed within the central aperture of the shell, and a core rotatably disposed within the central aperture. The syringe may further include a needle fluidically connectable to the inlet of the shell.

The shell may include an inlet, a follower extending into the central aperture, a first chamber defined within a thickness of the shell, a first chamber inlet fluidically connecting the first chamber to the central aperture of the shell, and a first chamber outlet fluidically connecting the first chamber to the central aperture of the shell. The first chamber may be at least partially filled with a lysis buffer.

The plunger may include a profiled portion disposable within the central aperture to engage the follower of the shell to cause a rotational displacement about the longitudinal axis when the plunger is displaced along the longitudinal axis.

The core may include a membrane disposed within the core, a first channel disposable to form a fluidic connection between the inlet of the shell and the first chamber inlet, and a second channel disposable to form a fluidic connection between the first chamber outlet and the membrane.

According to various embodiments, the shell may further include a second chamber defined within a thickness of the shell, a second chamber inlet fluidically connecting the second chamber to the central aperture of the shell, and a second chamber outlet fluidically connecting the second chamber to the central aperture of the shell. The core may further include a first expandable cavity; a third channel disposable to form a fluidic connection between the membrane and the second chamber inlet, and a fourth channel disposable to form a fluidic connection between the second chamber outlet and the first expandable cavity. The plunger may further include a first prong disposable within the first expandable cavity. The second chamber may be at least partially filled with a washing buffer.

The shell may further include a third chamber defined within a thickness of the shell, a third chamber inlet fluidically connecting the third chamber to the central aperture of the shell, a third chamber outlet fluidically connecting the third chamber to the central aperture of the shell, and optionally an outlet. The core may further include a second expandable cavity; a fifth channel disposable to form a fluidic connection between the second expandable cavity and the third chamber inlet, and optionally a fifth channel disposable to form a fluidic connection between the third chamber outlet and the outlet of the shell. The plunger may further include a second prong disposable within the second expandable cavity.

According to various embodiments, the syringe may further include a check valve disposed between the inlet and the first chamber, the check valve being oriented to limit backflow from the first chamber toward the inlet.

Various embodiments relate to a method for separating nucleic acids from a blood sample, the method comprising drawing the blood sample from a patient using the syringe according to any of the embodiments described herein.

Various embodiments relate to a system comprising a syringe, according to any of the embodiments described herein and a portable PCR device adapted to receive nucleic acids from the syringe. The system may further include a needle fluidically connectable to the inlet of the shell.

Various embodiments relate to a method for detecting an agent in a sample, using the system according to any of the embodiments described herein. The method may include separating nucleic acids from a blood sample by drawing the blood sample through the syringe; and testing the nucleic acids in a portable PCR device to detect the agent.

These and other features, aspects, and advantages of various embodiments will become better understood with reference to the following description, figures, and claims.

BRIEF DESCRIPTION OF THE FIGURES

Many aspects of this disclosure can be better understood with reference to the following figures.

FIG. 20A is an example according to various embodiments illustrating a photograph of a filter housing.

FIG. 20B is an example according to various embodiments illustrating a photograph of a filter chamber.

FIG. 20C is an example according to various embodiments illustrating a photograph of an assembled syringe comprising a filter housing and a filter chamber.

FIG. 20D is an example according to various embodiments illustrating a photograph showing a top view of the assembled syringe as shown in FIG. 20C.

FIG. 20E is an example according to various embodiments illustrating a photograph of the assembled syringe as shown in FIG. 20C in a first configuration.

FIG. 20F is an example according to various embodiments illustrating a photograph of the assembled syringe as shown in FIG. 20C in a second configuration.

FIG. 20G is an example according to various embodiments illustrating a photograph of a the filter housing as shown in FIG. 20A.

FIG. 21A is an example according to various embodiments illustrating a side view photograph of a cylindrical cam in a first position, the cylindrical cam comprising a plunger and a syringe body, the plunger having pins that engage a groove in the syringe body.

FIG. 21B is an example according to various embodiments illustrating a top view photograph of the cylindrical cam as shown in FIG. 21A in the first position.

FIG. 21C is an example according to various embodiments illustrating a side view photograph of the cylindrical cam as shown in FIG. 21A in a second position.

FIG. 21D is an example according to various embodiments illustrating a top view photograph of the cylindrical cam as shown in FIG. 21C in the second position.

FIG. 21E is an example according to various embodiments illustrating a side view photograph of the cylindrical cam as shown in FIG. 21A in a third position.

FIG. 21F is an example according to various embodiments illustrating a top view photograph of the cylindrical cam as shown in FIG. 21E in the third position.

FIG. 21G is an example according to various embodiments illustrating a side view photograph of the cylindrical cam as shown in FIG. 21A in a fourth position.

FIG. 21H is an example according to various embodiments illustrating a top view photograph of the cylindrical cam as shown in FIG. 21G in the fourth position.

Figure 1:
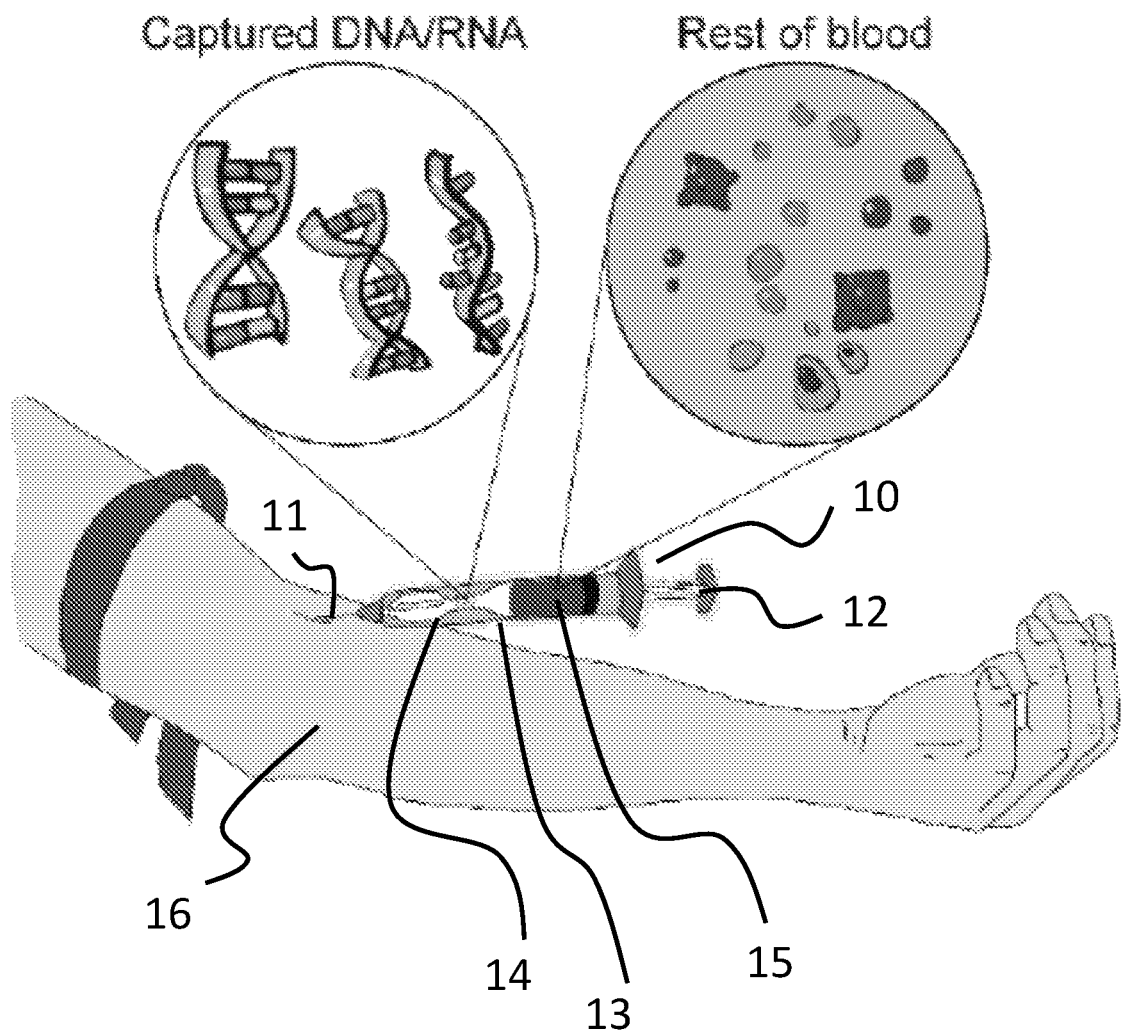
FIG. 1 is an example according to various embodiments, illustrating an integrated syringe capable of simultaneously drawing blood and purify DNA/RNA.

It should be understood that the various embodiments are not limited to the examples illustrated in the figures.

DETAILED DESCRIPTION

Introduction and Definitions

Various embodiments may be understood more readily by reference to the following detailed description. Unless defined otherwise, all technical and scientific terms used herein have the same meaning as commonly understood by one of ordinary skill in the art to which this disclosure belongs.

As used herein, the term "standard temperature and pressure" generally refers to 25° C. and 1 atmosphere. Standard temperature and pressure may also be referred to as "ambient conditions." Unless indicated otherwise, parts are by weight, temperature is in ° C., and pressure is at or near atmospheric. The terms "elevated temperatures" or "high-temperatures" generally refer to temperatures of at least 100° C.

The term "mol percent" or "mole percent" generally refers to the percentage that the moles of a particular component are of the total moles that are in a mixture. The sum of the mole fractions for each component in a solution is equal to 1.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

Unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

The examples and embodiments described herein are for illustrative purposes only and that various modifications or changes in light thereof will be suggested to persons skilled in the art and are to be included within the spirit and purview of this application. Many variations and modifications may be made to the above-described embodiment(s) of the disclosure without departing substantially from the spirit and principles of the disclosure. All such modifications and variations are intended to be included herein within the scope of this disclosure.

General Discussion

Various embodiments relate to a new blood-sampling syringe that fully incorporates a nucleic acid purification function. One innovation of various embodiments is to integrate a cylindrical cam design in a diagnostic tool. Various embodiments may use the vacuum created by a plunger in a syringe to continuously perform blood lysis, silica absorption, and washing tasks. According to various embodiments, a simple draw of blood from patients may result in a completely prepared sample that is ready for nucleic acid detections. This approach has not been previously attempted for diagnostic purposes and it could potentially transform current medicine in handling infectious disease by automating the labor-intensive sample preparation. For seamless and comprehensive operation with a single pull of the plunger, various embodiments utilize a cylindrical cam mechanism in the plunger to translate the linear plunger-pulling motion to actuate valving that automatically switches between the lysis task to the washing task. Since the integrated syringe, according to various embodiments, may be unpowered and may require no external supplies, the devices may be quickly adapted by any medical personnel in low-resource settings. Various embodiments of the syringe may be readily and inexpensively mass produce, adding minimal cost to aid global health.

Various embodiments relate to nucleic acid detection using a real-time reverse-transcription polymerase chain reaction (rRT-PCR) device. The eluted sample may be mixed with chemical reagents which enable nucleic acid detection, such as real-time reverse-transcription polymerase chain reaction (rRT-PCR). The rRT-PCR method is a robust and reliable technique that converts target RNA to complementary DNA (cDNA) and amplifies the target cDNA sequence while monitoring a signal originating from intercalating probes to quantify the amount of cDNA being amplified. rRT-PCR can be performed with custom-designed primers to provide highly specific diagnosis by amplifying a specific sequence of RNA. This enables multiplexed detection with the capability of differentiating various types of infections, including ZIKV, DENV, and CHIKV, to coordinate proper treatment. The use of complex reagents in real-time PCR is an obstacle disabling this high-quality assay in a remote clinic. To produce pre-mixed reagents which are stable in room temperature, lyophilization can be used. Lyophilization is a process used to produce pills for most drugs including ibuprofen and acetaminophen by rapidly drying the chemical compounds into a solid form to increase the stability of the reagents at room temperature and prevent degradation.

Figure 2:
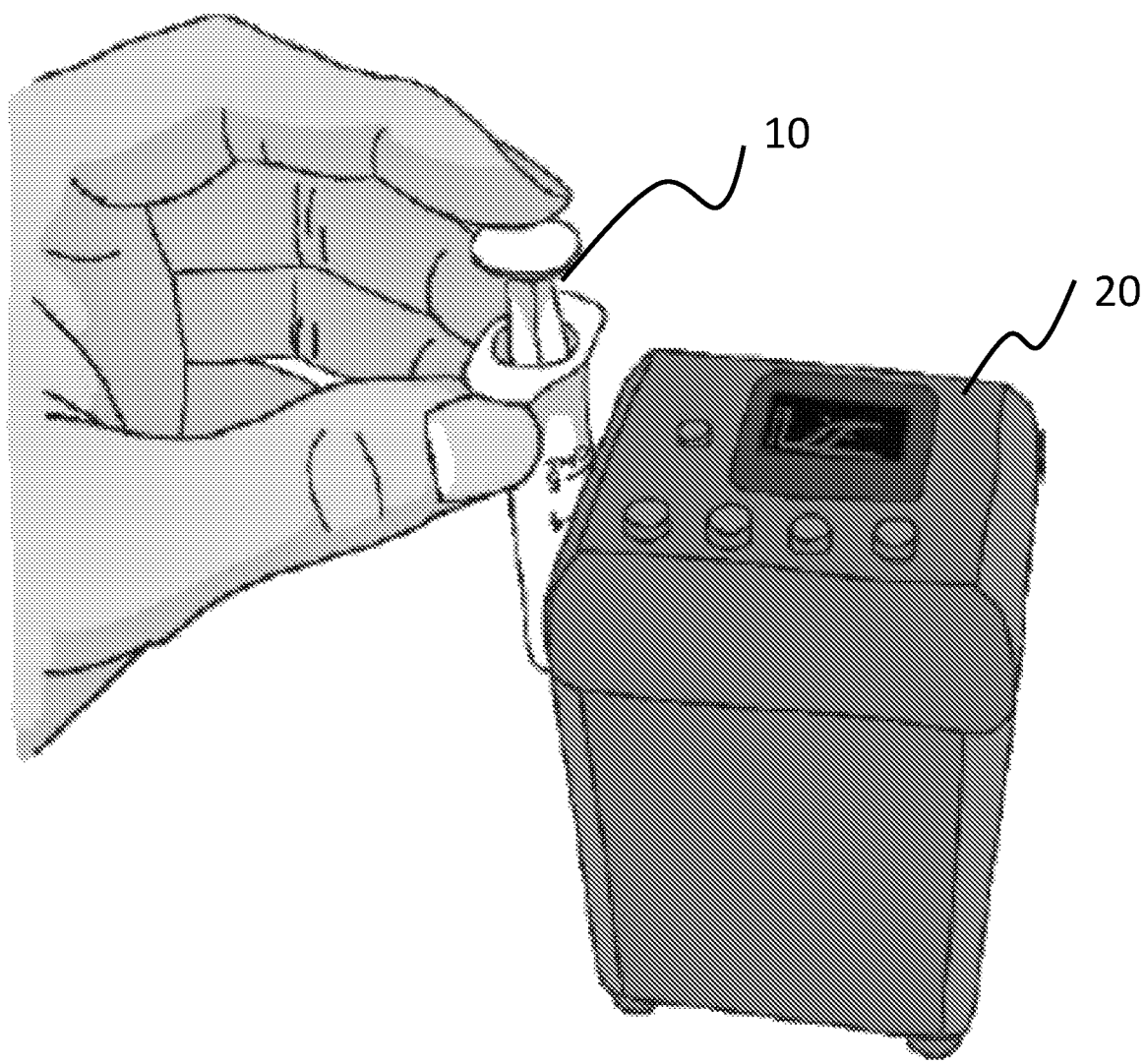
FIG. 2 is an example according to various embodiments, illustrating a direct use of an integrated syringe with a real-time PCR device for simple plug-in operation.

FIGS. 1 and 2 provide an overview of a sample collect-purify integrated syringe and a real-time PCR device according to various embodiments. More specifically, FIG. 1 is an example according to various embodiments, illustrating an integrated syringe capable of simultaneously drawing blood and purifying DNA/RNA. As shown in FIG. 1, an integrated syringe 10, having a needle 11, a plunger 12, and a cylindrical housing 13, may be used to withdraw a blood sample from a patient 16. According to various embodiments, the needle 11 may be omitted or replaced by another selective inlet apparatus, such as for example, a pipette. The blood need not be drawn directly from a patient 16, but may alternatively be drawn through the syringe from an intermediate container. The housing 13 may include a first section 14 and a second section 15. DNA/RNA may be captured by mechanisms provided within the first section 14 of the housing 13. Blood remaining after DNA/RNA has been captured in the first section 14 may be collected in a reservoir in the second section 15. FIG. 2 is an example according to various embodiments, illustrating a direct use of an integrated syringe 10 with a real-time PCR device 20 for simple plug-in operation.

Various embodiments enable multiplexed rRT-PCR-based diagnosis for ZIKV, DENV, and CHIKV, while simplifying the rRT-PCR-based diagnosis using an innovative syringe design and real-time PCR device to facilitate a wider usage of rRT-PCR-based diagnosis in smaller clinics and remote medical operations. Various embodiments provide a comprehensive two-step diagnosis platform for infectious disease, which covers tasks from blood collection and sample preparation to nucleic acid amplification and detection/quantification. By using the proposed devices, a clinician may simply draw blood from the patient 16 using the integrated syringe 10 and insert the syringe into the real-time PCR device 20 for multiplexed diagnosis of ZIKV, DENV, and CHIKV using rRT-PCR. The result of the detection will indicate the type of infection as well as the severity of infection. According to various embodiments, an appropriate treatment may be provided to the patient within a time period from the blood collection. The time period may be within a range having a lower limit and/or an upper limit. The range may include or exclude the lower limit and/or the upper limit. The lower limit and/or upper limit can be selected from about 30, 35, 40, 45, 50, 55, 60, 65, 70, 75, 80, 85, 90, 95, 100, 105, 110, 115, 120, 125, 130, 135, 140,145, 150, 155, 160, 165, 170, 175, 180, 185, 190, 195, and 200 minutes. For example, according to certain embodiments, the time period may be less than about 2 hours, or any combination of lower limits and upper limits described. Furthermore, according to various embodiments, the appropriate treatment may be provided within the time period with little involvement of highly-trained clinicians and without any delay due to long transportation and processing of the sample at a centralized laboratory.

The proposed integrated syringe, according to various embodiments, may have several unique advantages compared to traditional sample processing methods and devices. The integrated syringe, according to various embodiments, may be completely passive and may require no electricity or power. The integrated syringe may be a self-contained device that collects and processes samples directly from patients. Long-term transportation without decay may be enabled by purifying the sample immediately upon collection and prior to beginning transportation. No prior training is required for users of devices according to various embodiments, because the design is familiar, resembling a typical syringe. The device, according to various embodiments, may be easily mass produced for inexpensive distribution. For at least these reasons, various embodiments may make a transformative impact to global health in handling infectious disease diagnosis by enabling early-stage diagnostics and assisting in limiting epidemics.

Various embodiments relate to a new blood-sampling syringe that fully incorporates a nucleic acid purification function. A cylindrical cam design may be integrated into the blood-sampling syringe, adding additional functional as a diagnostic tool. Vacuum may be created by the plunger in the syringe to continuously perform blood lysis, silica absorption, and washing tasks. A simple draw of blood from patients may result in a completely prepared sample that is ready for nucleic acid detections. For seamless and comprehensive operation with a single pull of the plunger, various embodiments provide a cylindrical cam mechanism in the plunger of the syringe to translate the linear plunger-pulling motion to actuate valving that automatically switches between the lysis task to the washing task. Because the integrated syringe is unpowered and requires no external supplies, the device may be quickly adapted by any medical personnel in low-resource settings.

Various embodiments further relate to a small, handheld, and robust real-time PCR device, capable of multiplexed detection of ZIKV, DENV, and CHIKV, developed to work directly with the integrated syringe. Previously, portable PCR devices have been reported, but a PCR device is only an amplification tool for DNA/RNA and relies on additional scientific tools such as gel electrophoresis to provide information on the amplified DNA, thus inapplicable for simplifying the workflow of nucleic acid-based diagnosis. In contrary, the real-time PCR device incorporates fluorescence molecules which directly report the detail information of amplified DNA. Various embodiments provide one of the smallest real-time PCR devices reported to date. The real-time PCR device is designed to work without external power for several hours and is simple to operate by inserting the integrated syringe and a cartridge. The real-time PCR device according to various embodiments may be capable of analyzing nucleic acid amplifications to determine the quantity of pathogenic nucleic acid in the sample to reveal the stage of infection. The portable, handheld real-time PCR device may be fabricated with low-cost materials to allow mass production at low cost and enable a large distribution of the device.

The tools, according to various embodiments, are expected to enable the sophisticated, and accurate PCR-based diagnosis in low-resource setting at low cost. Various embodiments provide a comprehensive two-step diagnosis platform, including an integrated syringe, real-time PCR device, and cartridges. The platform may be operated by simply drawing blood from a patient and inserting the syringe into the real-time PCR device, which may result in a transferring of purified viral RNAs from the syringe into the cartridge. The cartridge may hold lyophilized real-time PCR reagents to enable nucleic acid amplification as soon as the RNA is eluted into the cartridge. The two-step diagnosis platform may provide the capability of comprehensively replicating the standard infectious disease diagnosis process currently used in clinics and hospitals. A variety of benefits may be enabled by the automation of sample preparation in the syringe. Previous studies on the logistics of diagnostics have indicated that the diagnostic tool still needs to be operated by practitioners, nurse or medical assistant, who can draw blood and prescribe the appropriate medicine after the diagnosis. Thus, the proposed devices are intended to be used by medical staffs at a remote clinic which suffers from a lack of diagnostic tools for the quick turnaround in treatments. Various embodiments may be used to assist preventing and managing epidemics. Although the present disclosure describes ZIKV, DENV, and CHIKV diagnostics in particular, it will be readily appreciated by a person having ordinary skill in the art that the proposed tools may be easily applied or modified to detect other infectious diseases, such as HIV and malaria, for example, by modifying the primer in rRT-PCR.

Figure 3:
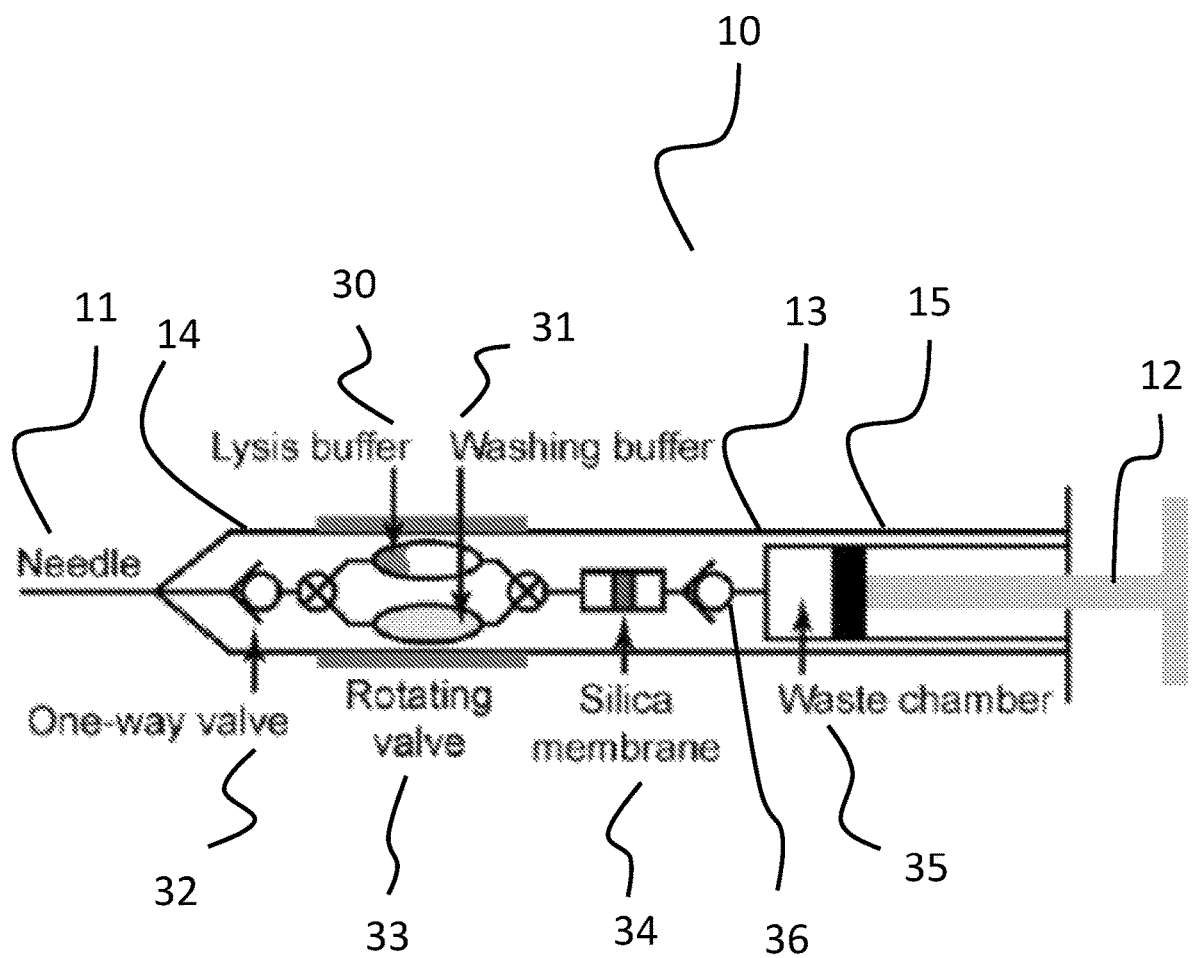
FIG. 3 is an example according to various embodiments, illustrating a integrated syringe.
Figure 4:
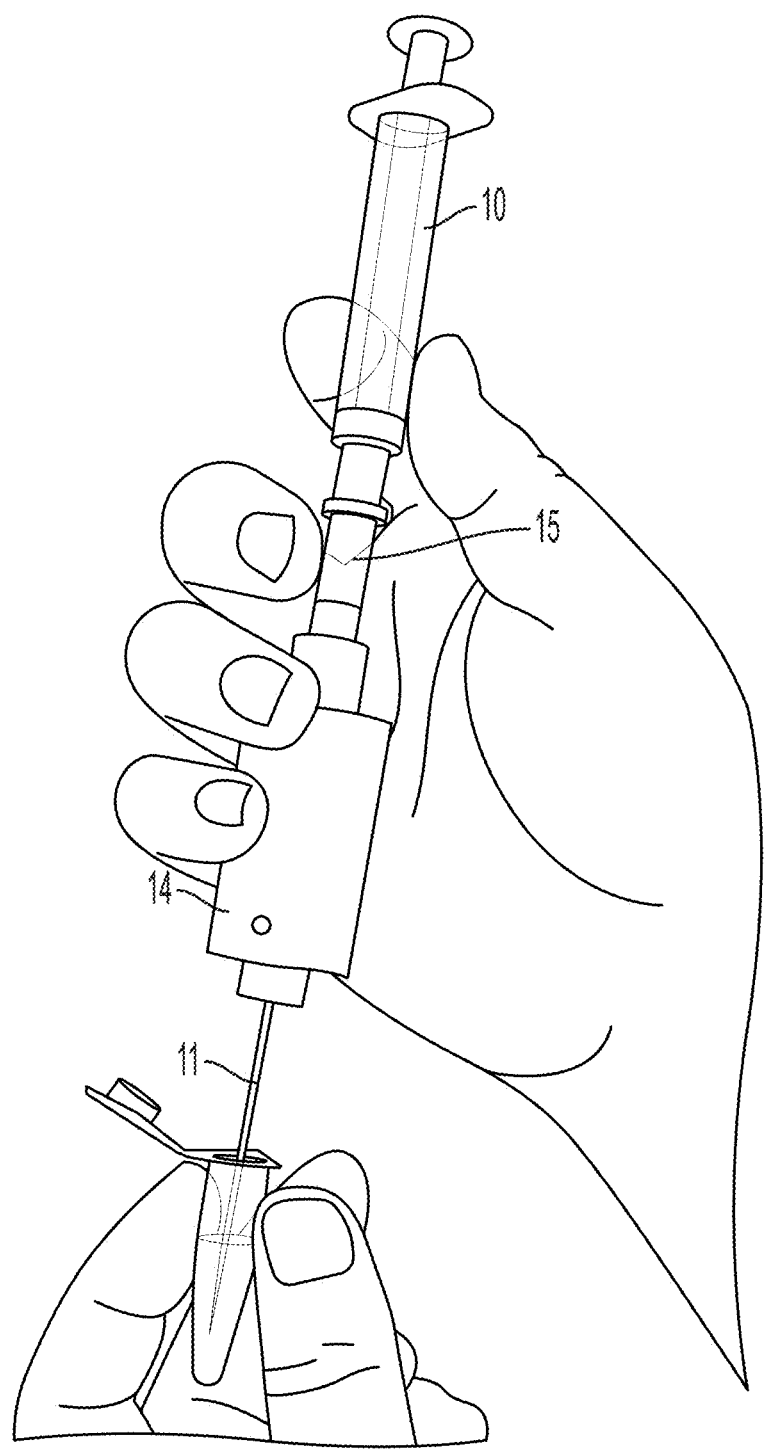
FIG. 4 is an example according to various embodiments, illustrating a photograph of a collect-purify syringe device.
Figure 5:
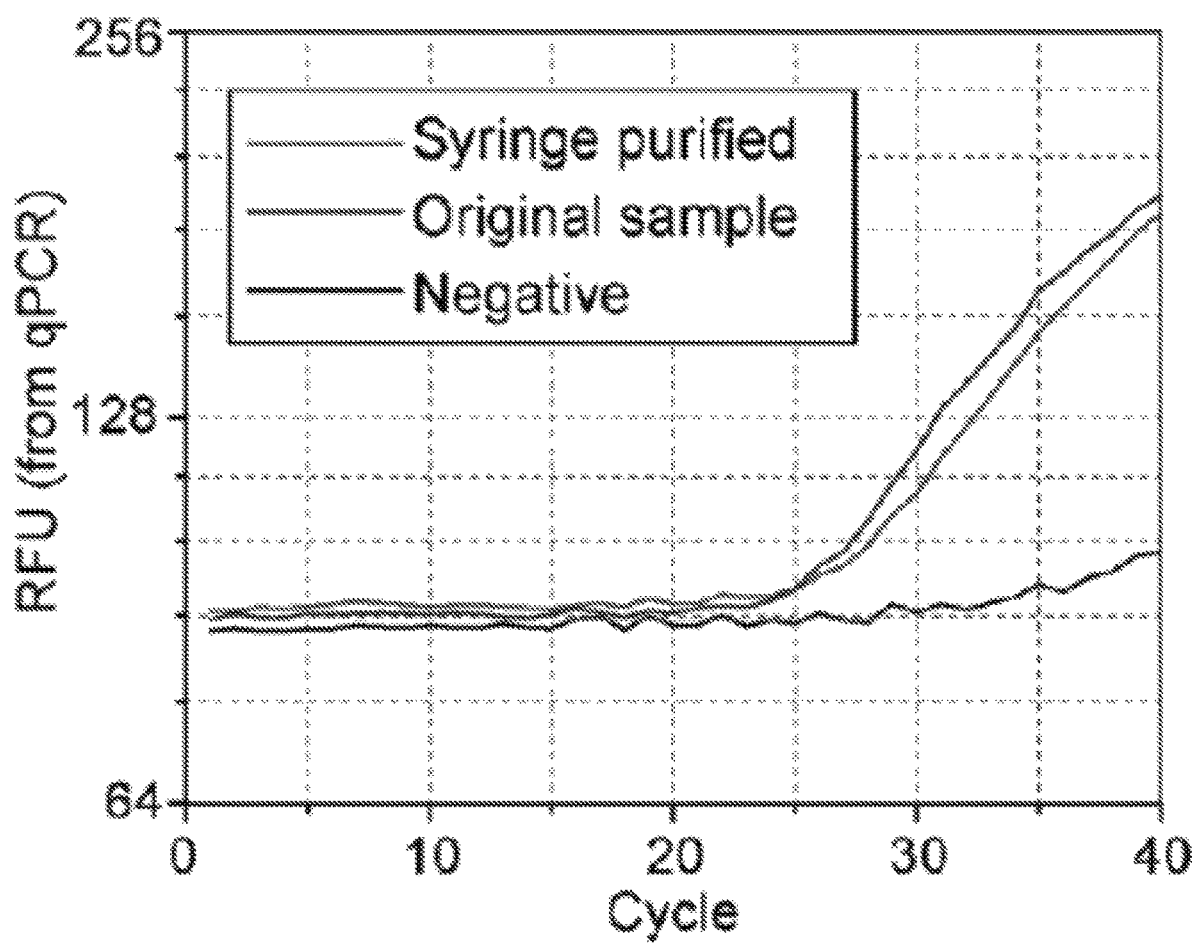
FIG. 5 is an example according to various embodiments, illustrating a chart showing the high efficiency of the syringe on target DNA from DNA-spiked whole blood using real-time PCR.

FIGS. 3, 4, and 5 illustrate a sample collect-purify syringe design according to various embodiments. FIG. 3 is an example according to various embodiments, illustrating an integrated syringe 10. The integrated syringe 10 may include a needle 11, a plunger 12, and a cylindrical housing 13. The housing 13 may include a first section 14 and a second section 15. DNA/RNA may be captured by mechanisms provided within the first section 14 of the housing 13. For example, according to various embodiments, DNA/RNA may be specifically binding in the silica membrane 34 that is illustrated in FIG. 3. Blood remaining after DNA/RNA has been captured in the first section 14 may be collected in a waste chamber 35 in the second section 15. More specifically, blood entering the housing 13 via the needle 11 may pass through a one-way valve 32 and into a rotating valve assembly 33. The rotating valve assembly 33 may include a first chamber 30 that may include a lysis buffer and a second chamber 31 that may include a washing buffer. According to various embodiments, the washing buffer may be a solvent such as ethanol. As used herein, a "lysis buffer" is a buffer solution used for the purpose of breaking open cells for use in molecular biology experiments that analyze the labile macromolecules of the cells. According to various embodiments, the washing buffer may be a detergent such as a sodium dodecyl sulfate (SDS) lysis buffer and/or Triton X-100. SDS is ionic denaturing detergent. Hot SDS buffer is often used when the proteins need to be completely solubilized and denatured. A typical Triton X-100 lysis buffer may have a composition of 50 mM Tris-HCl, 150 mM NaCl, 1% Triton X-100 and, 5 mM EDTA. According to various embodiments, the lysis buffer may be an ionic denaturing detergent or a nonionic detergent. As will be described herein, DNA/RNA may be captured in this first section 14. A membrane 34 may be disposed between the first section 14 and the second section 15. The membrane 34 may comprise silica. Blood may be filtered through the silica membrane which promotes the capturing of DNA by silica absorption. The mechanism behind DNA adsorption onto silica is not fully understood; without wishing to be bound by theory, one possible explanation involves reduction of the silica surface's negative charge due to the high ionic strength of the buffer. This decrease in surface charge leads to a decrease in the electrostatic repulsion between the negatively charged DNA and the negatively charged silica. Meanwhile, the buffer also reduces the activity of water by formatting hydrated ions. This leads to the silica surface and DNA becoming dehydrated. These conditions lead to an energetically favorable situation for DNA to adsorb to the silica surface. An additional one-way valve 36 may be disposed between the membrane 34 and a waste chamber 35 in the second section 15.

FIG. 4 is an example according to various embodiments, illustrating a photograph of a collect-purify syringe device 10, having a first section 14, a second section 15, and a needle 11. As illustrated by FIG. 4, the first section 14 and the second section 15 do not necessarily need to be housed in a single housing 13.

Still referring to FIGS. 3 and 4, the integrated syringe 10 may simultaneously perform blood draw and DNA purification. For example, in preliminary study, a syringe 10 as shown schematically in FIG. 3 and photographically in FIG. 4, was preloaded with washing buffer in the second chamber 31 and the blood was lysed using lysis buffer in the first chamber 30. As whole blood spiked with pathogenic DNA was drawn into the syringe 10 by pulling the plunger 12, the blood was filtered through the silica membrane 34 which promotes the capturing of DNA by silica absorption. Subsequently, the rotating valve 33 was turned to engage the second chamber 31 preloaded with washing buffer into the path of the silica membrane 34. With the continuous pull of the plunger 12, the washing buffer ran through the silica membrane 34, washing away the component of blood which did not bind strongly to the membrane 34. Results are presented in FIG. 5, which is an example according to various embodiments, illustrating a chart showing the high efficiency of the syringe on target DNA from DNA-spiked whole blood using real-time PCR. In qPCR data, the number of cycle when the signal starts to creep up (also known as Ct) indicates how many DNA molecules are present in the qPCR sample. In this case, syringe purified sample closely matches that of original DNA sample. This means that the syringe purification was able to collect most of DNA present in the blood sample. More specifically, the effectiveness of DNA capture after the washing step, described above with respect to FIGS. 3 and 4, was confirmed by quantifying the captured DNA using real-time PCR and comparing to the quantification of the original blood sample.

Various embodiments relate to an integrated syringe system that includes a cylindrical cam mechanism. FIGS. 6, 7, 8, 9, 10, and 11 illustrate a proposed cam mechanism to synchronize the pulling of a plunger to various actuations of mechanisms with the integrated syringe system. More specifically, various embodiments relate to a blood-sampling syringe that incorporates, and optionally fully houses, a spin column-based nucleic acid purification module. The syringe according to various embodiments may provide a step similar to each step of the benchtop sample preparation protocol required for RNA capture and recovery, including but not limited to: blood lysis, silica binding, repeated washings, and elution. The ability to process RNA is particularly useful for diagnosing ZIKV, CHIKV, and DENV (which all contain RNA). According to various embodiments, the syringe may also be employed to process DNA. Indeed, according to various embodiments, any blood-borne disease may be processed using the device.

Figure 6:
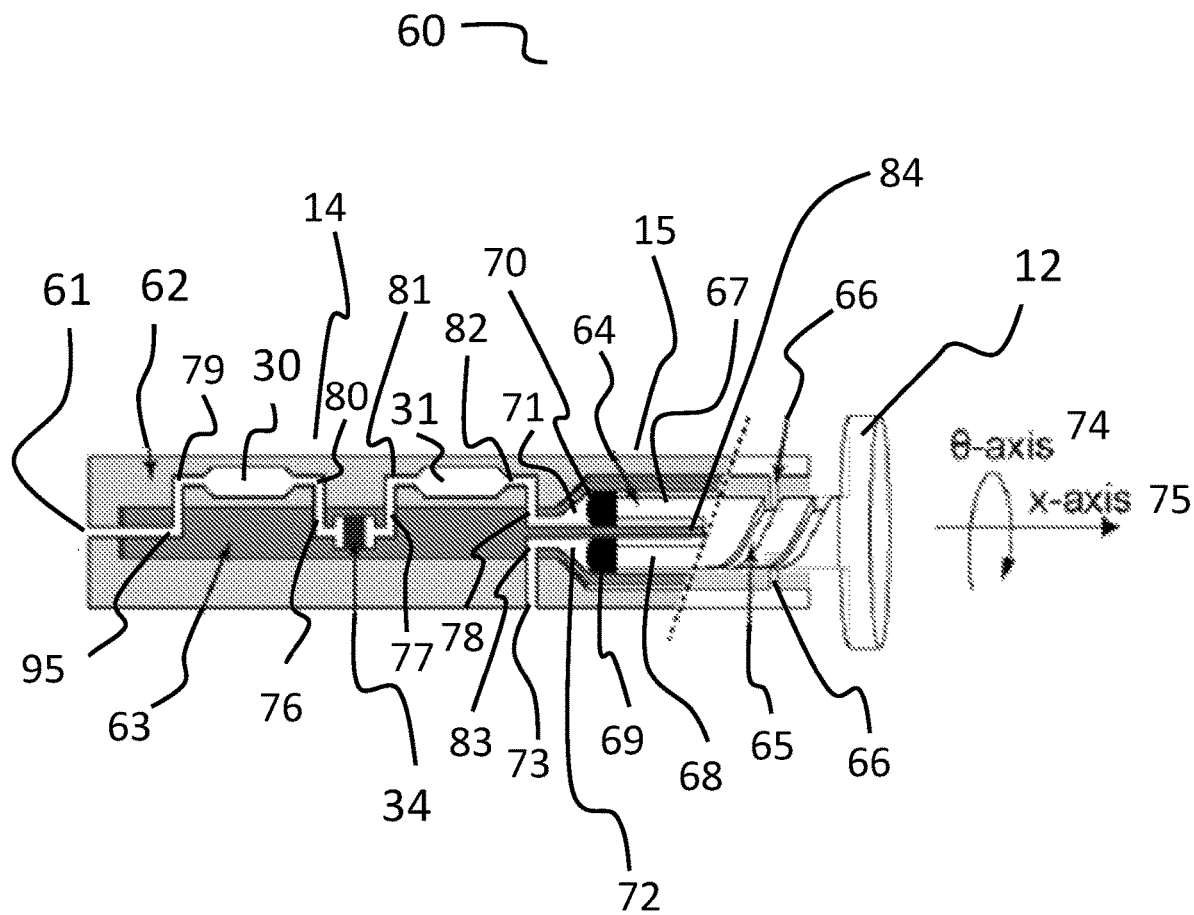
FIG. 6 is an example according to various embodiments, illustrating a cam mechanism to synchronize plunger pulling to actuations.

FIG. 6 is an example according to various embodiments, illustrating a cam mechanism 60 to synchronize pulling actions of plunger 12 to actuations of mechanisms of components of the integrated syringe 10 (not shown in FIG. 6). The syringe 60 may include a shell 62 defining a central aperture extending through a longitudinal x-axis 75 of the integrated syringe 10. The cam mechanism 60 may have an approximately cylindrical shape. The central aperture may include cylindrical sections and optional one or more frustoconical sections. A diameter of the central aperture may vary along the longitudinal x-axis 75, such that in the first section 14, the central aperture may generally have a smaller diameter than in the second section 15. A frustoconical section may provide a taper from the diameter of the central aperture in the first section 14 to the diameter of the central aperture in the second section 15. The shell 62 may include define a plurality of chambers within a wall thickness thereof, including but not limited to the first chamber 30 that may include the lysis buffer and the second chamber 31 that may include the washing buffer. Each chamber may have an inlet and an outlet. Both the inlet and the outlet of each chamber may provide a fluidic pathway connecting the chamber to the central aperture. For example, the first chamber 30 may have a first chamber inlet 79 providing a fluidic pathway connecting the first chamber 30 to the central aperture of the shell 62. Similarly, the second chamber 31 may have a second chamber inlet 81 and a second chamber outlet 82 connecting the second chamber 31 to the central aperture of the shell 62. The first chamber 30 and the second chamber 31 may both be defined within the first section 14 of the shell 62. The shell 62 may further include an inlet 61 defining a fluidic pathway into the central aperture of the shell 62. For example, the inlet 61 may provide a fluidic pathway to a needle (not shown). The cam mechanism 60 may further include a core 63 disposed within the central aperture of the shell 62. The core 63 may be sized to conformingly fit within the central aperture of the shell 62 while also being rotatable within the central aperture of the shell 62. The conforming fit should be tight enough to prevent fluid leakage when fluid flows through the connections to be described hereinafter. According to various embodiments, an o-ring (not shown) may be incorporated to minimize or to prevent leakage. The core 63 may include a first channel 95 that is sized and is positionable to provide a fluidic connection between the inlet 61 of the shell 62 and the first chamber inlet 79 to allow a fluid, such as blood, to flow from the needle (not shown) through the inlet 61, through the first channel 95, through the first chamber inlet 79 and into the first chamber 30. The core 63 may further include a second channel 76 sized and positionable to provide a fluidic connection between the first chamber outlet 80 and a membrane 34 disposed within the core 63. The core 63 may further include a third channel 77 sized and positionable to provide a fluidic connection between the membrane 34 and the second chamber inlet 81. The core 63 may still further include a fourth channel 78 sized and positionable to provide a fluidic connection between the second chamber outlet 81 and a first expandable cavity 71 defined within the core 63. The core 63 may also include a second expandable cavity 72 that is adjacent to the first expandable cavity, but separated therefrom by a boundary wall 84. The core 63 may further include a fifth channel 83 sized and positionable to provide a fluidic connection between the second expandable cavity 72 and an outlet 73 defined in the shell 62. The first expandable cavity 71 and the second expandable cavity 72 may be expandable or contractable based on operation of the plunger 12, which may be disposed therein. More specifically, the plunger 12 may have a first prong 64 having a first gasket 70 disposable within the first expandable cavity 71. The plunger 12 may also have a second prong 68 having a second gasket 69 disposable within the second expandable cavity 72. Upon sufficient extension of the plunger 12 such that the first gasket 70 and the second gasket 69 are displaced beyond the boundary wall, a fluidic connection may be made between the first expandable cavity 71 and second expandable cavity 72. These dual barrels (the first prong 64 with first gasket 70 and second prong 68 with second gasket 69 operating in conjunction the first expandable cavity 71 and the second expandable cavity 72 respectively) allow clean elution without contamination from the waste. For more details regarding the dual barrels used for elution, see FIG. 11.

The plunger 12 may include a profiled section 65, such as a threading. The profiled section 65 may engage with a follower 66 defined within the central aperture of the shell 62. When the plunger 12 is moved along the longitudinal x-axis 75 engagement of the profiled section 65 and the follower 66 may cause the shell 62 and the core 63 to rotate relative to one another about the Θ-axis 74. Rotation about the Θ-axis 74 may cause sequential engagements, in any order, of the first channel 95 with the first chamber inlet 79, of the first chamber outlet 90 with the second channel 76, of the third channel 77 with the second chamber inlet 81, of the second chamber outlet 82 with the fourth channel 78, and/or of the fifth channel 83 with the outlet 73. As already noted, the shell may include any desired number of chambers, similar to the first chamber 30 and the second chamber 31. Each of such chambers may have inlets and outlets and corresponding channels in the core 63 may be provided. The pull of the plunger 12 in the x-axis 75 may cause Θ to change based on the engraved profile on the plunger 12 surface to synchronize the rotating valve with each sample preparation task associated with each of such chambers. In general, the rotating valve may comprise the first channel 95, the second channel 76, the third channel 77, and the fourth channel 78. Therefore, the rotating valve may be positioned within core 63.

Figure 7:
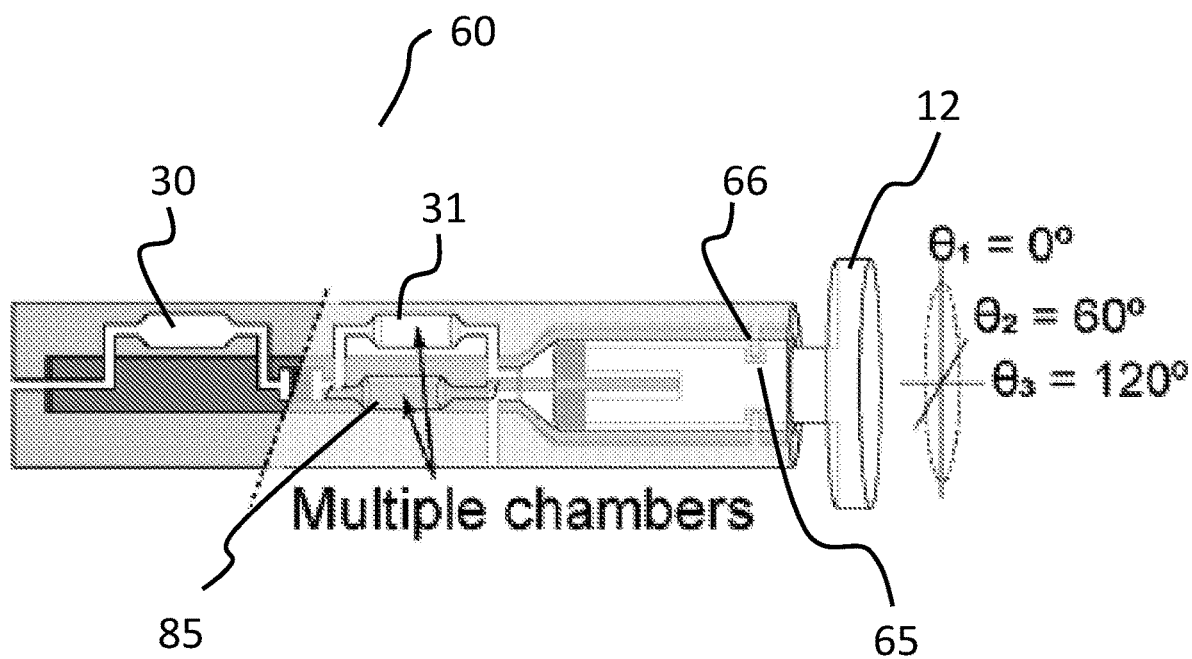
FIG. 7 is an example according to various embodiments, illustrating a cam mechanism to synchronize plunger pulling to actuations.

FIG. 7 is an example according to various embodiments, illustrating a cam mechanism 60 to synchronize plunger 12 pulling to actuations. The cam mechanism 60 on the plunger 12 with the follower 66 and profile 65 translates x-axis movements to a rotations. Multiple chambers, for lysis (first chamber 30), washing (second chamber 31), and elution (third chamber 85), are positioned in different Θs. For more details regarding third chamber 85 used for elution, see FIG. 11.

Figure 8:
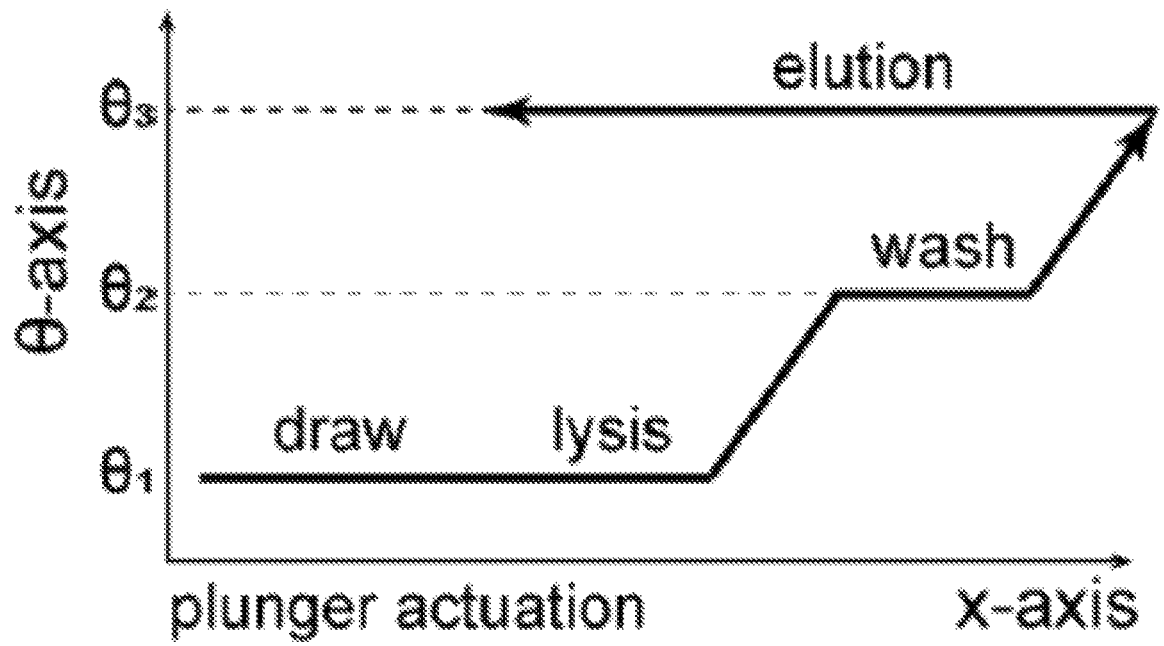
FIG. 8 is an example according to various embodiments, illustrating a chart showing a profile that synchronizes the simple pull to various tasks by automatically rotating the valve to $\Theta 1$, $\Theta 2$, and $\Theta 3$.

FIG. 8 is an example according to various embodiments, illustrating a chart showing a profile 65 of the plunger 12 that synchronizes the simple pull to various tasks by automatically rotating the valve to Θ1, Θ2, and Θ3. The profile, which enables the specific sequence of tasks, may be mathematically calculated against the x-, and Θ-axis and fabricated according to a variety of methods well-known to those of ordinary skill in the art. For example, the profile 65, along with all other components may be machined, injection molded, or produced via additive manufacturing techniques, such as 3D printing.

Figure 9:
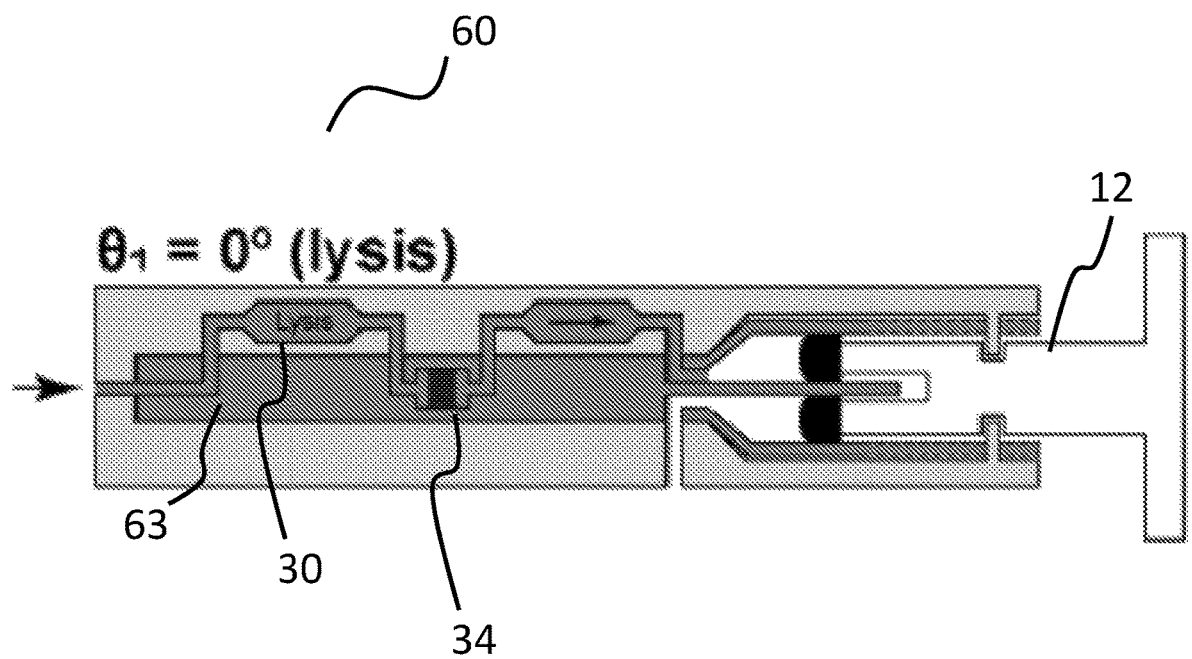
FIG. 9 is an example according to various embodiments, illustrating the cam mechanism to synchronize plunger pulling to actuations at a lysis step.
Figure 10:
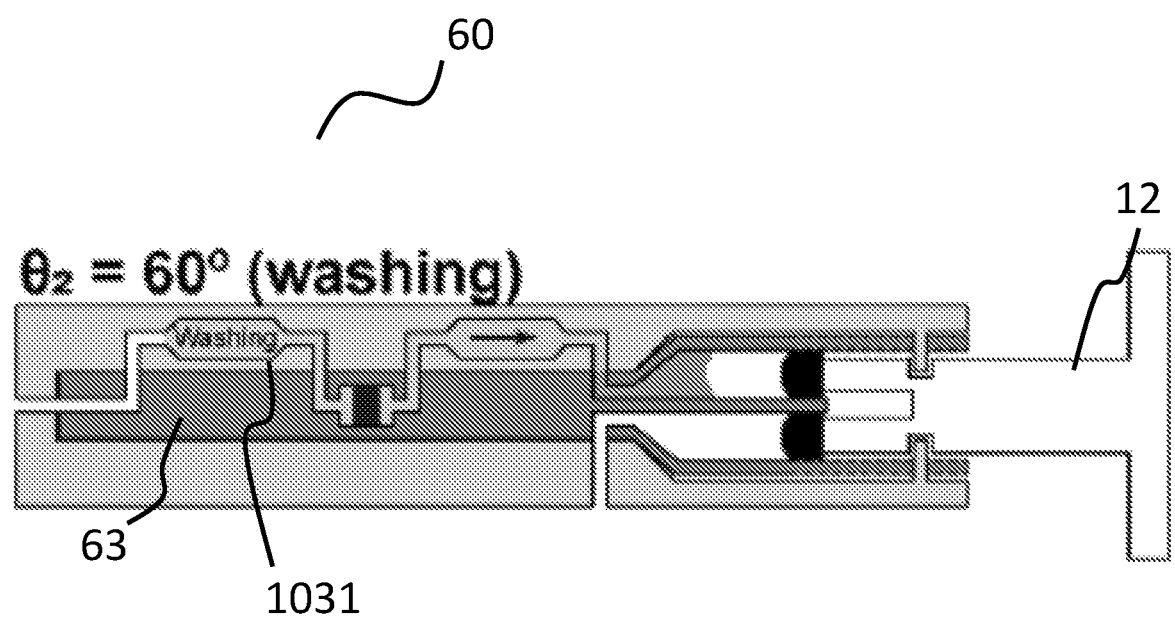
FIG. 10 is an example according to various embodiments, illustrating the cam mechanism to synchronize plunger pulling to actuations at a wash step.
Figure 11:
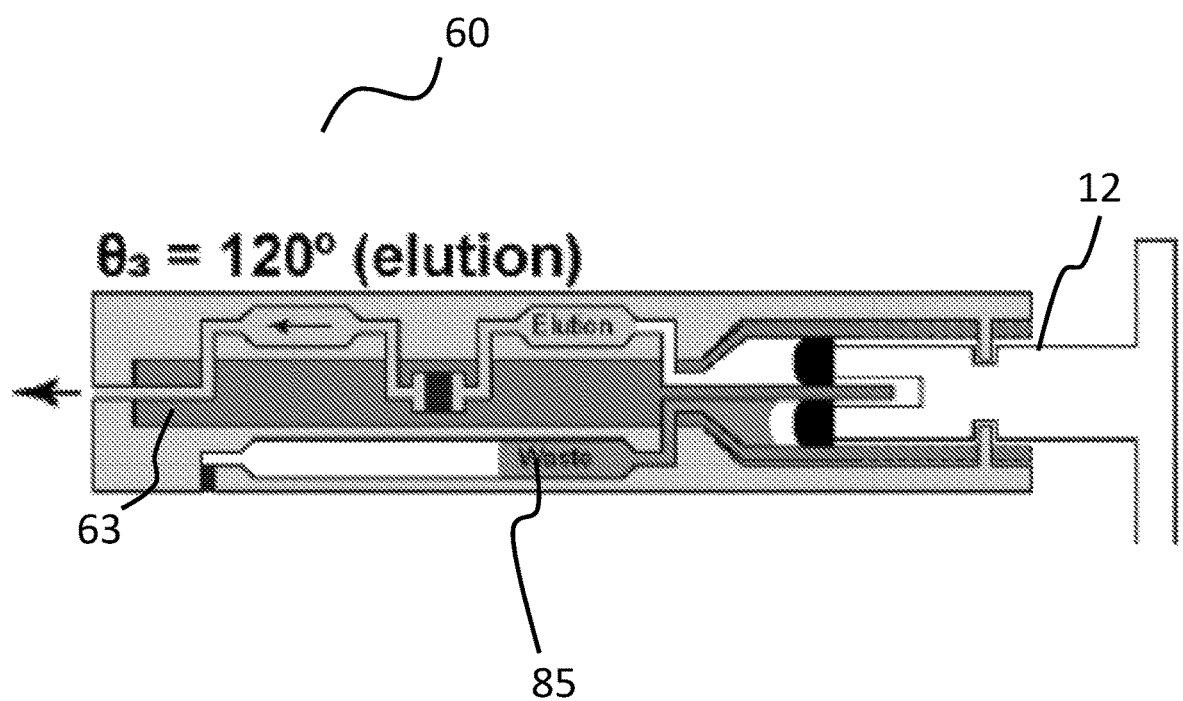
FIG. 11 is an example according to various embodiments, illustrating the cam mechanism to synchronize plunger pulling to actuations at an elution step.

FIGS. 9, 10, and 11 are an examples according to various embodiments, illustrating the cam mechanism 60 to synchronize plunger 12 pulling to actuations at a lysis step in which a fluidic connection is made to a first chamber 30, a wash step in which a fluidic connection is made to a second chamber 31, and an elution step in which a fluidic connection is made to a third chamber 85, respectively. During the initial pull of the plunger, the needle may draw blood into a lysis chamber, for example the first chamber 30 (FIGS. 9, 10, and 11, $\Theta 1=0°$). A lysis buffer held within the lysis chamber may contain an anticoagulant, such as, for example, ethylenediaminetetraacetic acid (EDTA), to prevent coagulation of blood. After a brief lysis step, the mixture of anti-coagulated blood and lysis buffer may flow through the silica membrane 34 in which all or at least a substantia portion of RNA is captured. The remainder of the fluid may be pulled into a waste chamber, for example the second chamber 1031, as shown in FIG. 10. Then, the cam mechanism 60 rotates the core member 63 and/or the plunger 12 to $\Theta 2=60°$ detach the lysis chamber and connect the washing chamber. The continuous pull of the plunger may force the washing buffer (ethanol) to run through the silica membrane, washing away all the unnecessary molecules which are weakly bound to the silica. The used washing buffer is then stored in the waste chamber. The cam mechanism rotates further and switches out the waste chamber to the elution chamber (FIGS. 8 and 9, 10, and 11, $\Theta 3=120°$). The extraction of RNA is completed. Practical and safety aspects of the device will be considered; for example, the syringe will be designed with an ejection button to safely eject the needle once the collection has been completed. When the sample is ready to be eluted to a real-time PCR device, the plunger is pushed which causes the elution buffer (water) to run through the silica membrane toward the inlet of the syringe (where the needle was located before ejection). The elution buffer weakens the electrostatic binding of RNA to the silica membrane 34 and results in a release of RNA into the elution buffer. Using this method, the user only needs to pull the plunger 12 to draw blood and push the plunger 12 for elution.

Figure 12:
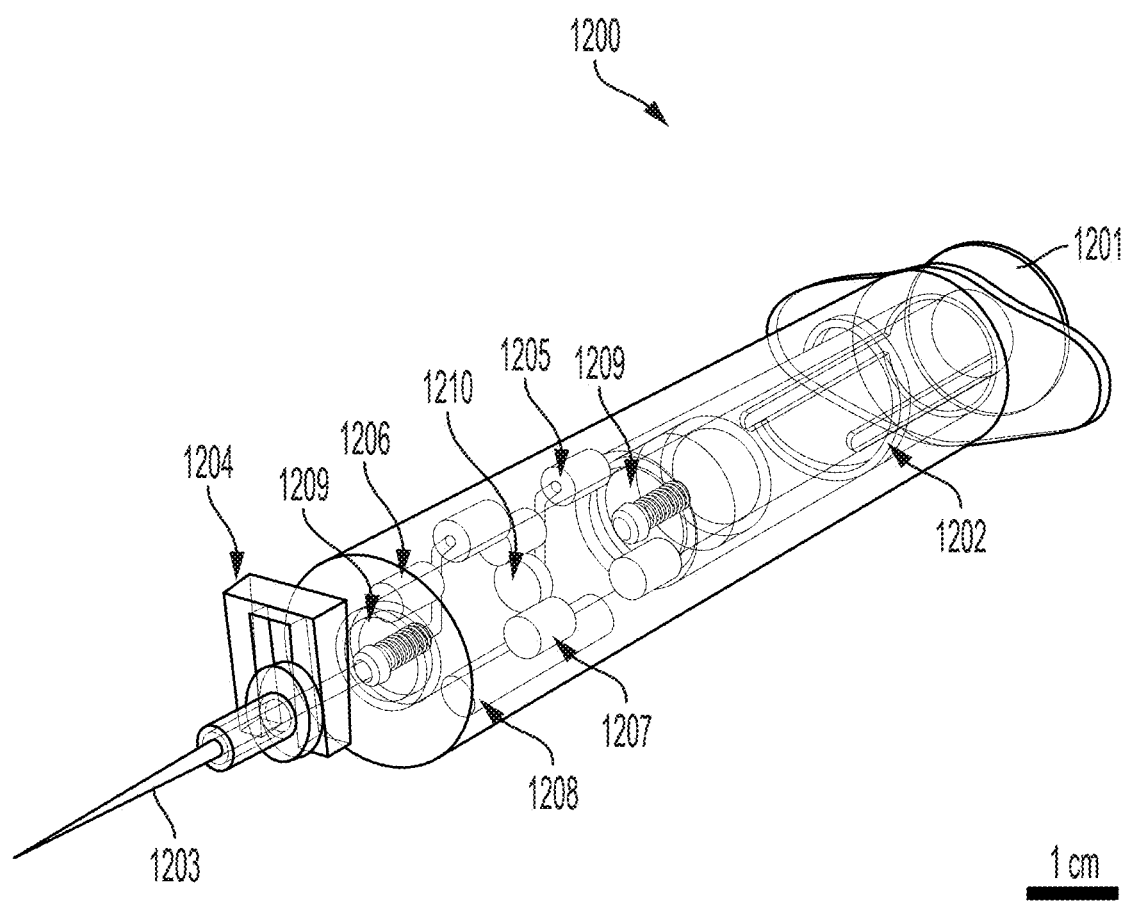
FIG. 12 is an example according to various embodiments, illustrating 3D SLA printing design of an integrated syringe.

FIG. 12 is an example according to various embodiments, illustrating 3D SLA printing design of an integrated syringe 1200. As described in various embodiments, the integrated syringe 1200 may include a plunger 1201, disposed within a body portion to form a cylindrical cam 1202. The integrated syringe 1200 may further include an ejectable needle 1203, which may be ejected using an ejection button 1204. As described according to various embodiments, the integrated syringe 1200 may include a plurality of chambers, such as for example an elution chamber 1205, a lysis chamber 1206, a washing chamber 1207, and a waste chamber 1208. The plurality of chambers may be interconnected in various configurations when the cylindrical cam 1202 is activated to twist the body portion thereby aligning various interconnecting channels. The various chambers and the interconnections may also be separated by one or more one-way valves 1209 and/or one or more membranes 1210, which may be any suitable type of membrane, for example a silica membrane.

Still referring to FIG. 12, and according to various embodiments, the syringe parts may be fabricated out of clear resin using a Stereolithography (SLA) 3D printer to test the optimal design (FIG. 12). The 3D-printed syringe may be tested for the long-term durability after the loading of lysis, washing, and elution buffers. The syringes may be preserved after the loading of buffers in various conditions: varying duration from days to a week, varying temperature (10-50° C.), and humidity (0-100%). Pictures may be taken for varying durations to monitor the possible leakage or drying of buffers. The selection of the lysis buffer, washing buffer, elution buffer, and silica membrane may be chosen from commercialized products which are highly optimized for silica-based RNA purification to mitigate risks. The needle-based mechanism in the integrated syringe may be useful if there is a blood collection specialist to perform the blood draw. The syringe design may be simply altered to use lower blood volume acquired by finger prick as an input, which would widen the usage of this technology. Additional modifications of the design will be readily apparent to persons having ordinary skill in the art based on the information provided in this disclosure. To reflect the goal of making a low-cost tool and estimate the cost per device for future production, feasibility studies may be conducted on every design iteration for plastic injection molding, an industrial standard for low-cost manufacturing.

It is possible to quantify nucleic acid purification efficacy of the integrated syringe. The optimal syringe design may be used to evaluate the efficacy of nucleic acid extraction and purification from whole blood purchased from Zen Bio Inc. Whole blood may be used with spiked ZIKV and DENV (ATCC VR-1843 and VR-1254). Because CHIKV requires a biosafety level 3 laboratory, it is possible to use CHIKV RNA (VR-3246SD). The efficacy of each step, lysis, washing, and elution may be tested both independently and collectively. The independent test may be conducted by isolating the specific step. For example, when testing the lysis step, only lysis might be performed using the integrated syringe and remaining steps may be carried out using reliable benchtop methods. This will help evaluate the effectiveness of the isolated step. Once all steps are independently examined, it is possible to test all the steps collectively. For quantification of each testing above, it is possible to use both real-time RT-PCR and gel electrophoresis using a benchtop real-time PCR machine (7900HT). The resulting Ct, the threshold cycle value which indicates the viral load, may be compared against the Ct measured from the spiked blood processed through gold standard benchtop methods, which are the spin column-based RNA purification (QIAamp RNA Blood Mini Kit) and magnetic RNA purification (MagMAX Blood RNA Isolation Kit). The anticipated data from Aim 1 b includes the percentage of RNA purification yield using a range of sample volumes from 100 μL to 1 mL of blood and the ratio between RNA recoveries of the integrated syringe and gold standard methods. The captured RNA may decay if the silica membrane retains RNase or may be inhibited from RT-PCR due to interferants. Thus, the washing step using ethanol may be crucial, according to various embodiments, in removing weakly bound RNase as well as PCR-inhibitory proteins in the membrane. Thus, it is also possible to measure RNA degradation after silica binding over time. RNA recovery yields of varied washing/lysis conditions will be measured. One goal, according to various embodiments, may be to closely match the efficacy of gold standard methods and produce a performance matrix of the proposed design. Silica membrane with a wide range of properties such as pore size will also be tested to ensure efficient RNA capture/extraction. The quantification experiments may, of course, be repeated for the iterative syringe design process to achieve optimal purification performance of the new collect-purify syringe.

Upon reviewing the present disclosure, a person having ordinary skill in the art will be able to perform a thorough development plan using SLA 3D printing to allow a quick turnaround between many iterative design processes. Anticipated failures may include (1) buffer leakage, (2) ineffective RNA capture in the silica membrane, and (3) insufficient washing after capture. Buffer leakage (1) may be managed by using an O-ring in mating parts and the thin coating of syringe parts with a hydrophobic film using polytetrafluoroethylene (PTFE) spray. Preliminary studies proved an efficient nucleic acid capture in the silica membrane. Thus, the risk of ineffective capture (2) is low. Insufficient washing can result in residual RNase, PCR-inhibitory proteins and interferants, and can cause an impeded amplification of cDNA, which will be clearly indicated in the real-time PCR data. If such results are observed, the washing buffer reservoir size may be increased to apply sufficient washing. With the successful demonstration of the preliminary data (FIGS. 3, 4, 5), such risks are well managed. The purchased blood may exhibit different properties compared to fresh blood because the purchased blood contains anti-coagulant. The syringe may be designed to add anti-coagulant (EDTA) as soon as the blood is drawn (as stated in Aim 1 a). This may convert fresh blood to anti-coagulated blood immediately. Thus, although it is possible to use anticoagulated blood for testing, the result may closely resemble using fresh whole blood. Persons having ordinary skill in the art will also be enabled by this disclosure to expand the testing to clinical trials using fresh whole blood directly from patients.

Various embodiments relate to a real-time polymerase chain reaction (PCR) device which directly uses the integrated syringe. FIGS. 13, 14, 15, and 16 illustrate a 3D manufactured real-time PCR device for rRT-PCR-based virus detection.

Figure 13:
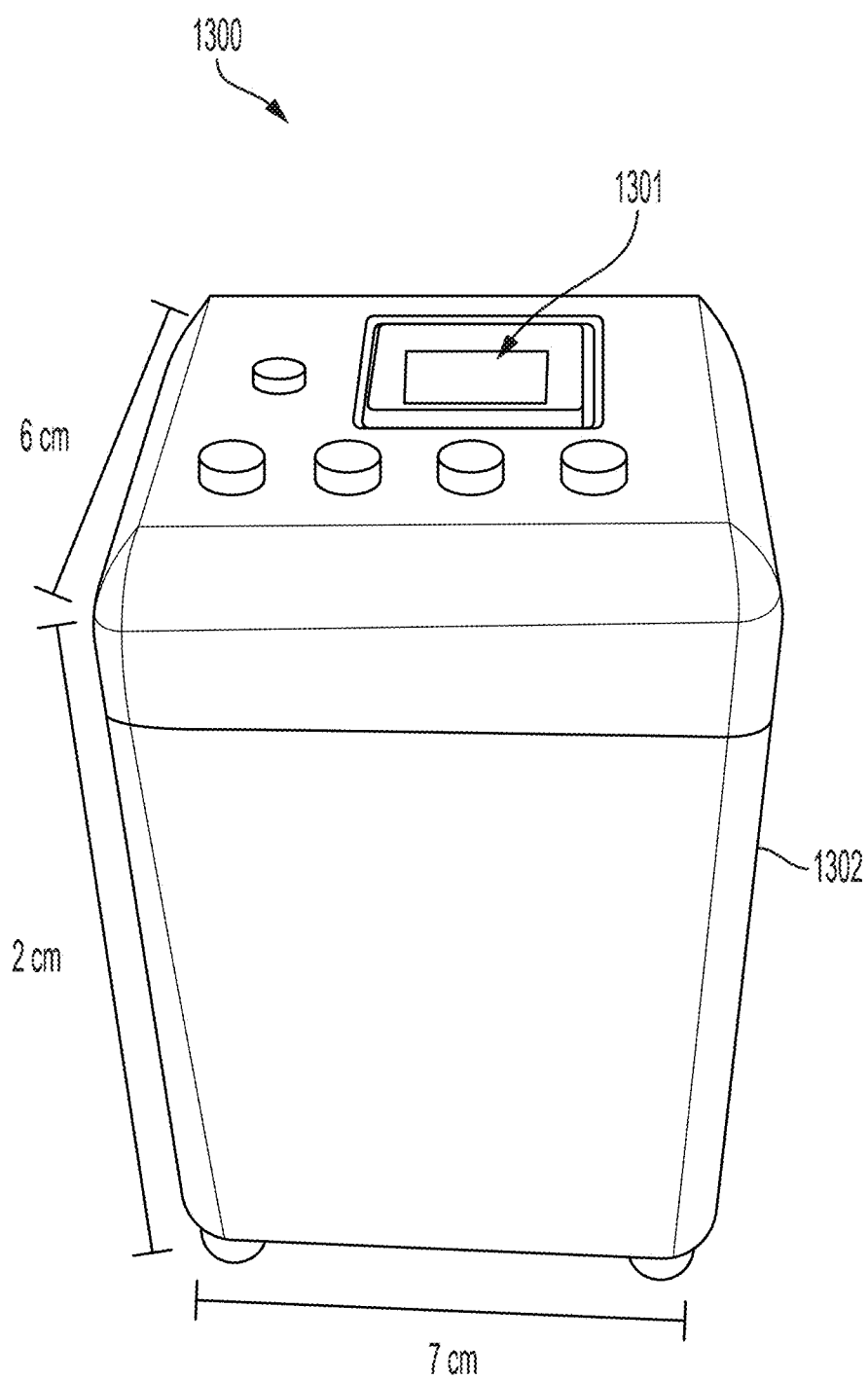
FIG. 13 is an example according to various embodiments, illustrating the amplification and fluorescence reading status displayed in real time.

FIG. 13 is an example according to various embodiments, illustrating the amplification and fluorescence reading status displayed in real time on a microview 1301 of an exemplary control assembly 1300, with a conveniently sized case 1302. The size of the case 1302 may be any suitable dimensions, for example about 2 cm by about 6 cm by about 7 cm.

Figure 14:
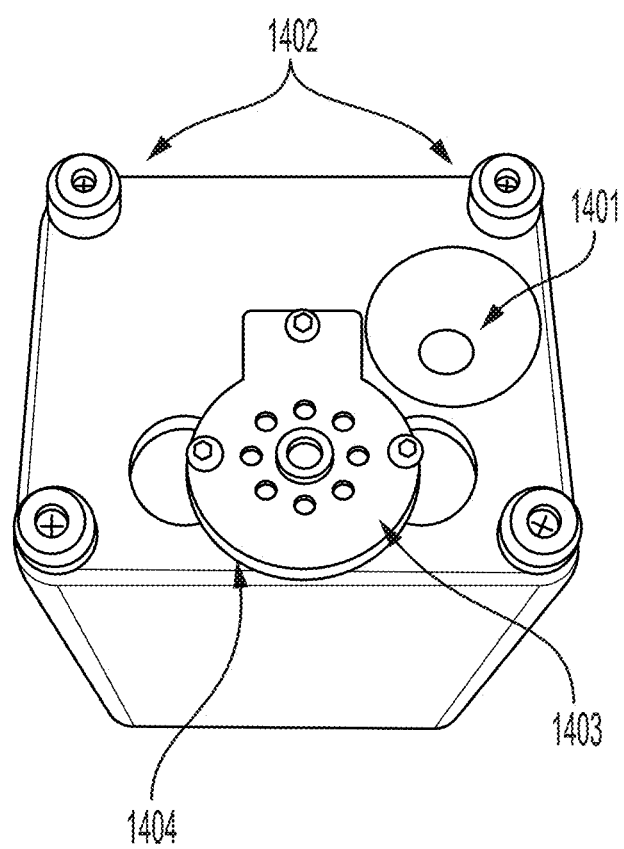
FIG. 14 is an example according to various embodiments, illustrating the bottom view showing an air inlet for the centrifugal fan.

FIG. 14 is an example according to various embodiments, illustrating a bottom view of the control assembly 1300 illustrated in FIG. 13, showing an air inlet 1401 for the centrifugal fan. As illustrated, the control assembly may include a plurality of spacers 1402, a bottom vent 1403, and a sample holder 1404.

Figure 15:
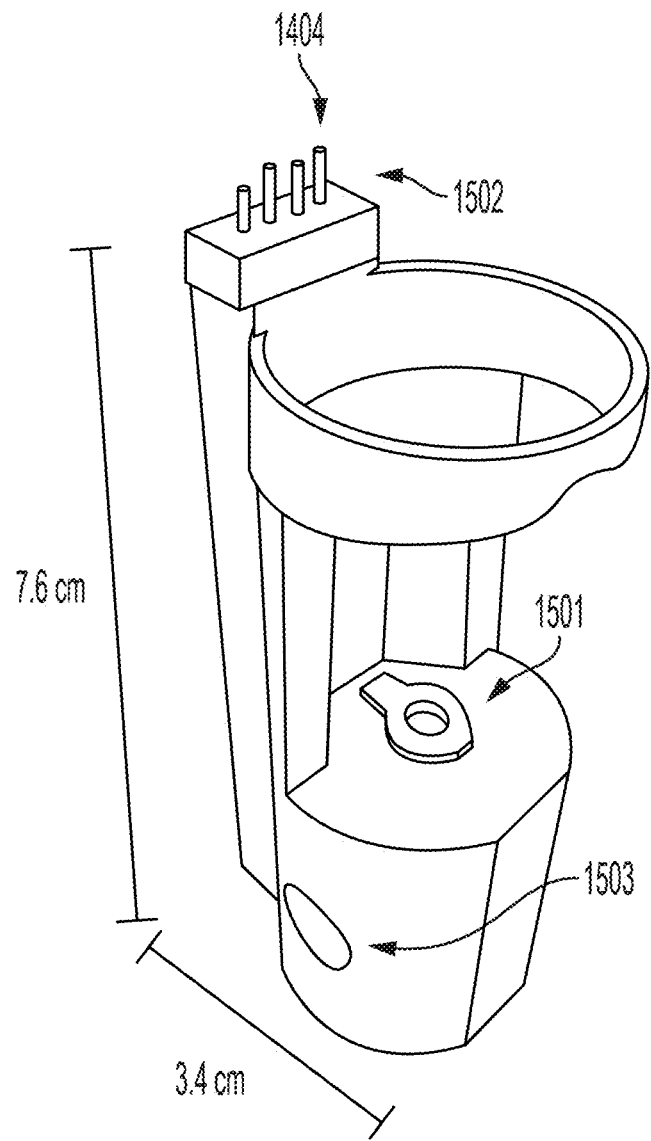
FIG. 15 is an example according to various embodiments, illustrating the sample holder holding a PCR tube.

FIG. 15 is an example according to various embodiments, illustrating the sample holder 1404 as illustrated in part in FIG. 14, holding a PCR tube 1501. The sample holder 1404 may further include one or more electrical contacts 1502 and an air inlet 1503. The sample holder may have any suitable dimensions, for example about 7.6 cm by about 3.4 cm. The dimensions may be readily adapted by those having ordinary skill in the art.

Figure 16:
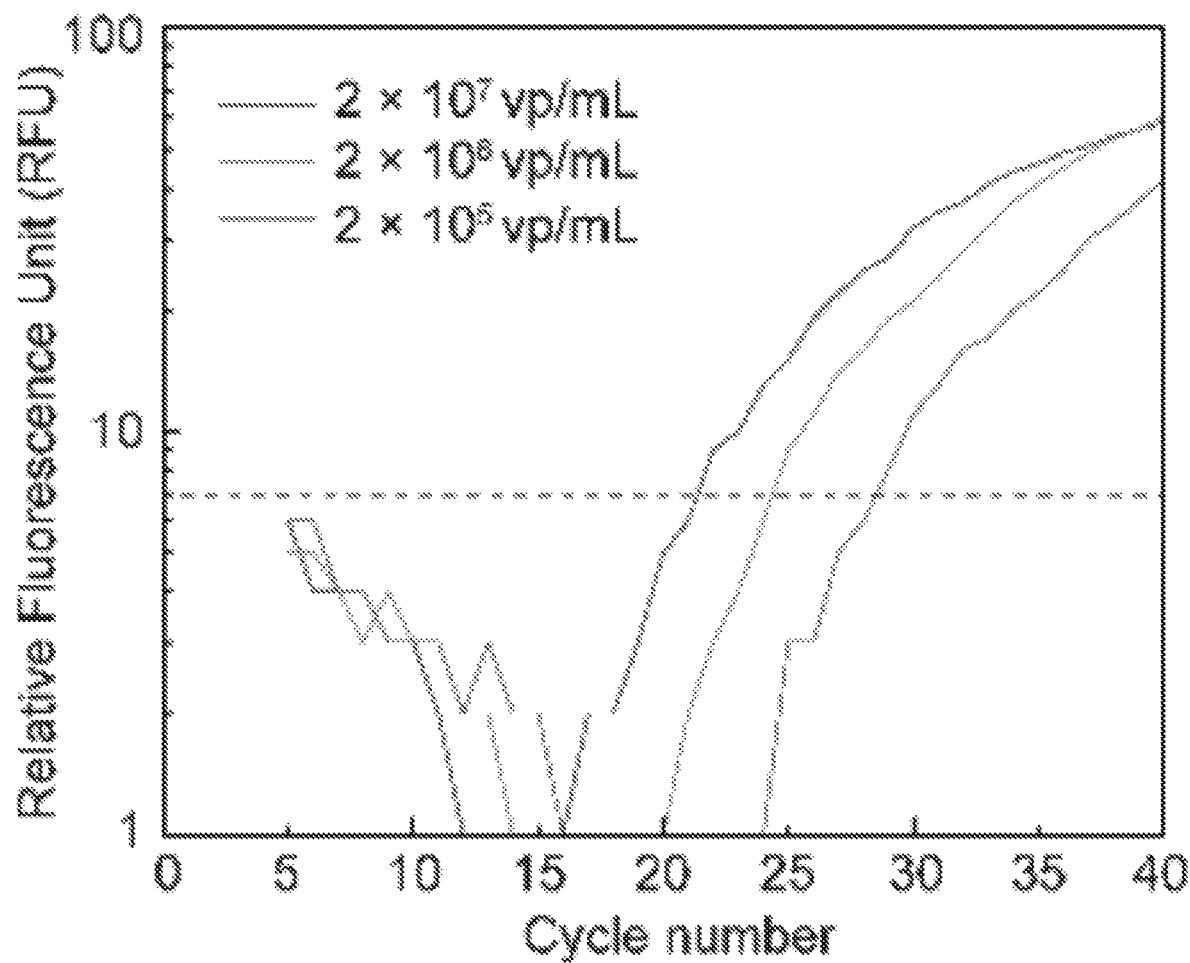
FIG. 16 is an example according to various embodiments, illustrating rRT-PCR Fluorescence readings showing the shift in the intensity measurements corresponding to the differing concentrations of virus.

FIG. 16 is an example according to various embodiments, illustrating rRT-PCR Fluorescence readings showing the shift in the intensity measurements corresponding to the differing concentrations of virus. In various embodiments, the PCR device may include a computing system 1900 depicted with reference to FIG. 23 or chip set 2000 depicted with reference to FIG. 24.

The high cost of real-time PCR machines has limited their accessibility to a centralized laboratory resulting in a long turnaround for diagnostics. Various embodiments relate to a set of 3D manufacturing methods for fabrication of a portable real-time PCR device (FIGS. 13, 14, and 15). The key advantage of this approach is the ability to upload the digital format of the design files to the internet for wide distribution, which people at any location can simply download and feed into their 3D printers for rapid manufacturing. The portable real-time PCR device designed using these methods is battery-operated, with a size of 12×7×6 cm$^3$ and weight of only 214 g. The production cost of the real-time PCR device was about 300 USD. The entire process of thermal cycling and time-coordinated fluorescence reading is automated by closed-loop feedback. The 3D-manufactured real-time PCR device was validated by detection of lentivirus, as a proxy for medically important retroviruses such as HIV. The Ct was measured from fluorescence recordings (FIG. 16). The device can operate for hours without any external power and demonstrated robust detection and quantitation of viral particles across a range of clinically relevant concentrations (FIG. 16). According to various embodiments, adaptation and refinement of this device for real-time PCR detection of samples purified using the integrated syringe may result in an innovative point-of-care system for infectious disease diagnosis. Various embodiments may further provide easy-to-use cartridges for multiplexed ZIKV, DENV, and CHIKV detection allowing users to simply plug in the cartridge and operate the device.

Figure 17:
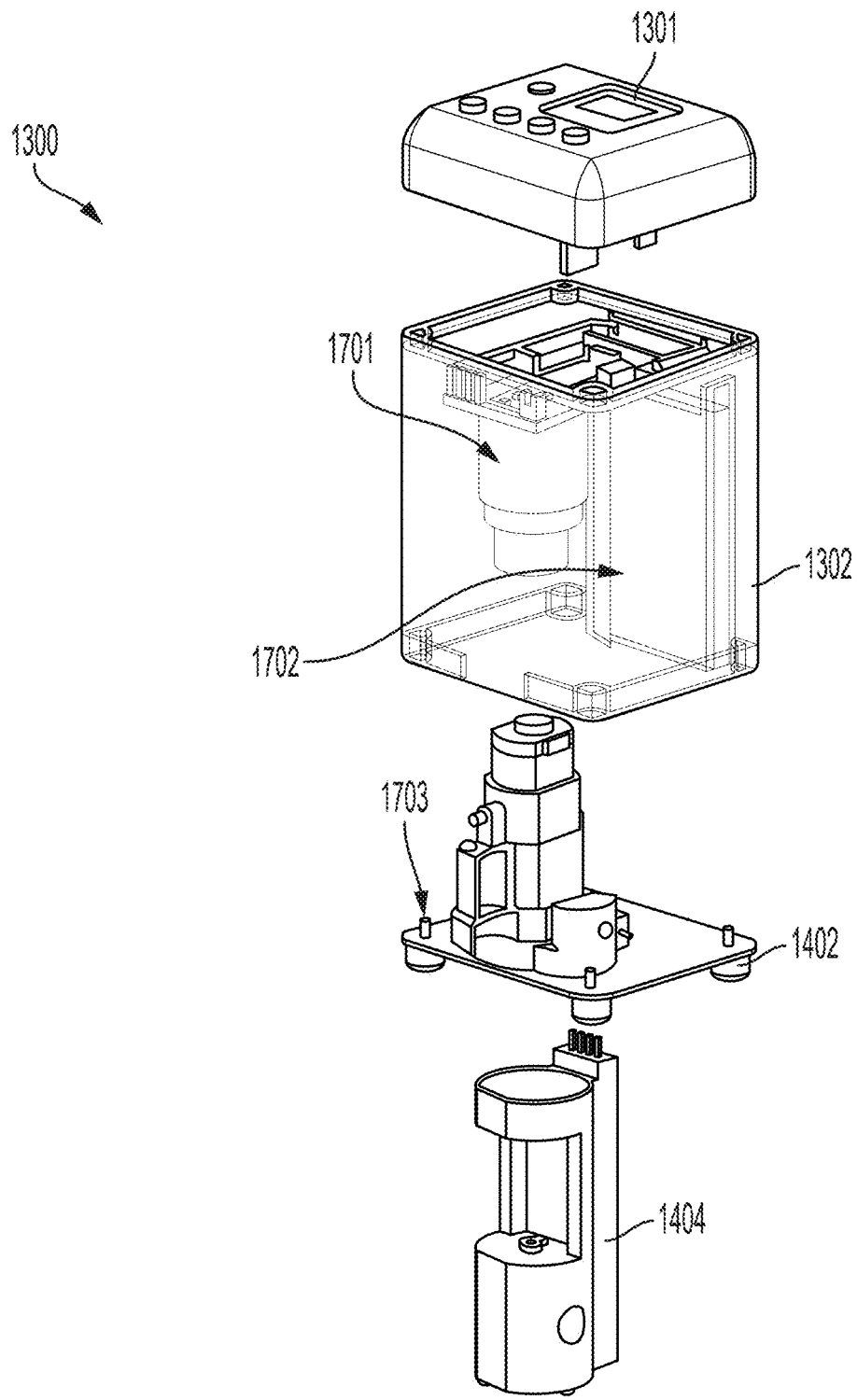
FIG. 17 is an example according to various embodiments, illustrating a 3D assembly of the two-tube real-time PCR system.

Upon reading the present disclosure persons having ordinary skill in the art will be readily equipped to fabricate and to test the real-time PCR device and cartridges. FIG. 17 is an example according to various embodiments, illustrating a 3D assembly of the two-tube real-time PCR system. As previously described, the control assembly 1300 may include a microview 1301, a case 1302, spacers 1402, and a sample holder 1404. FIG. 17 illustrates some additional details of the various components of the control assembly 1300, including an optical assembly 1701, batteries 1702, and bottom assembly 1703, as well as the interrelationships between these elements. The battery may be any suitable type of battery, for example a Li—Po battery.

Figure 18:
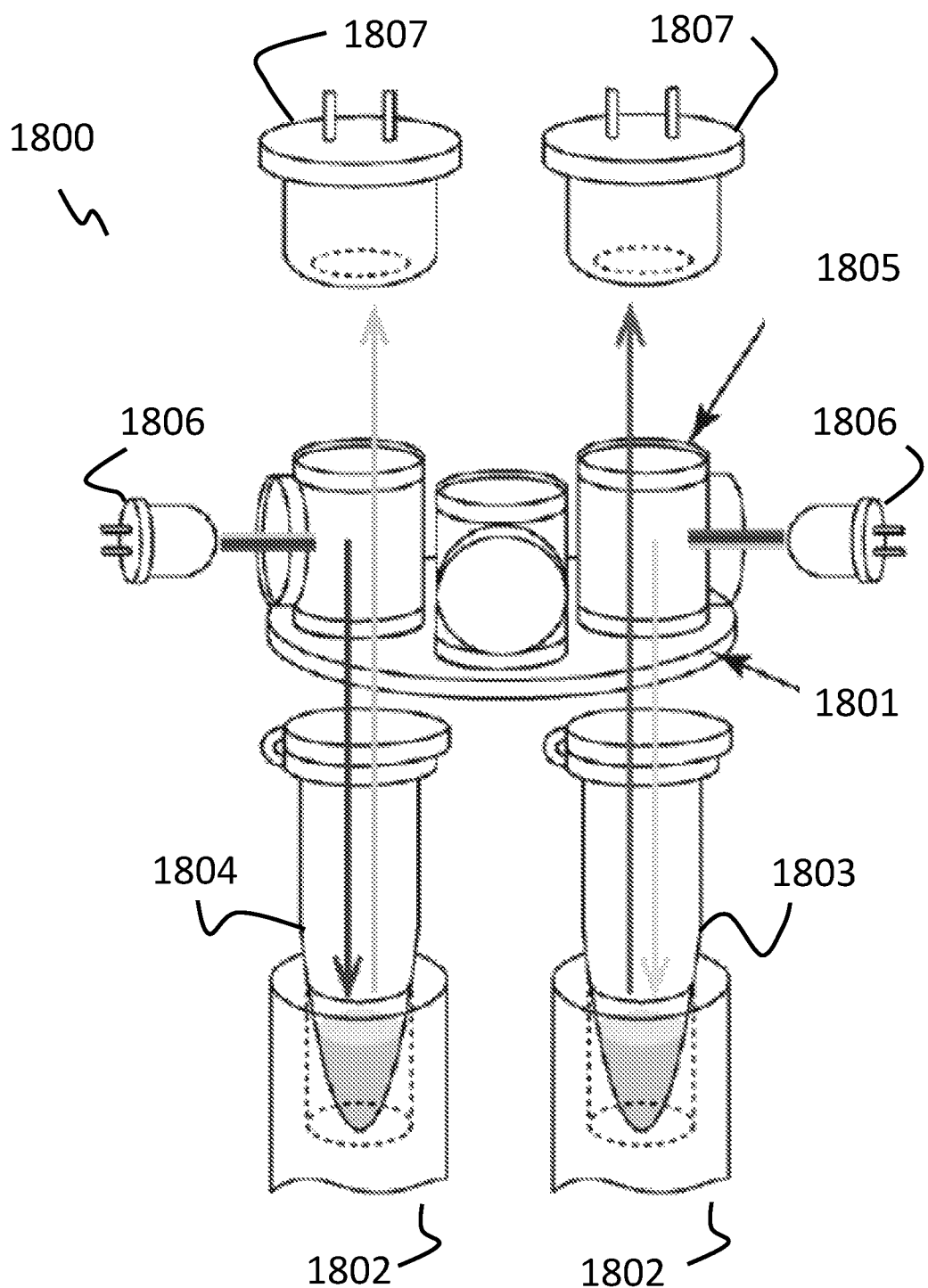
FIG. 18 is an example according to various embodiments, illustrating Fluorescence measurement using the filter turret to enable multiplexed detection.

FIG. 18 is an example according to various embodiments, illustrating a Fluorescence measurement using a filter turret 1801 to enable multiplexed detection. Various embodiments, therefore, relate to a real-time PCR device 1800 which may work with the integrated syringe to perform rRT-PCR. The portable real-time PCR detection system may be fabricated using an integration of optics, thermocycler, electronics, as previously demonstrated (FIGS. 17 and 18). Joule heating and convection-based cooling for thermocycling may be employed via heating elements 1802. Various embodiments of the real-time PCR device 1800 may be designed to incorporate a two-tube detection system to enable a simultaneous detection of an internal control and the sample from the integrated syringe. The two-tube detection system may include a control tube 1803 and a PCR tube 1804. With the increase in the thermal mass of the system due to two tubes, it is possible to explore other cooling options to manage the PCR reaction duration to be below 2 hours. Thermoelectric cooling using a Peltier device is a popular option when fast cooling is required. However, the Peltier cooler is power consuming and can use up to 200 Watts. High-density batteries (18650 battery with 6500 mAh) may be utilized to support the high-power operation of Peltier coolers. Four 18650 batteries can continuously run a 10 W Peltier for 6.5 hours. According to various embodiments it is also possible to use of thin-wall reaction tubes (later referred to as cartridge) to reduce the thermal mass. For quantitative PCR detections, optical setups 1805 for fluorescence measurements may be integrated (FIG. 17, optical assembly). The optical setups 1805 may include light filters and may further include white LEDs 1806. After each cycle, two photodiodes

1807 may take recordings of each tubes to show the level of Em: 520 nm), VIC (Ex: 538 nm, Em: 554 nm), and ABY (Ex: 560 nm, Em: 580 nm) fluorescence probes, respectively. White LEDs (2700 k) that emits broad excitation wavelength (500-650 nm) that is filtered through one of three filter sets which contain excitation, emission, and dichromic filters may be used. The band-pass of each excitation filters (Omega Optical: 475AF40, 525DF25, and 560DF10) are 455-495 nm (for FAM), 512.5-537.5 nm (for VIC), or 555-565 nm (for ABY). The excitation light is absorbed by the sample in the PCR tube, and subsequently emits light that is collected by an avalanche photodiode through emission filters (Omega Optical: 518.5AF17/M, 560DF10, and 580DF10), with a band-pass of 510-527 nm (for FAM), 555-565 nm (for VIC), or 575-585 nm (for ABY). Filter sets may be mounted on a motorized turret which allow for an automated change of filter sets between fluorescence measurements to enable multiplexed detection (FIG. 18). A single turret will be shared for two tubes to lower the cost of optical assembly as shown in FIG. 18. In a single PCR run, all three fluorescence probes (FAM, VIC, and ABY) corresponding to each disease (FAM: ZIKV, VIC: DENV, and ABY: CHIKV) may be measured. Following the PCR run, the Ct of each reaction may be automatically displayed based on the preset threshold level in the microcontroller's (MCU) embedded programming (FIG. 17, control assembly). Based on our preliminary design, it is possible to estimate the size and weight of the device to be 9 cm×6.5 cm×4 cm and about 300 g. The estimated cost for each device is about 300 USD. The cartridge may be designed to hold the lyophilized PCR reagents and internal control as well as to serve as a real-time PCR detection chamber. According to various embodiments, the cartridge holding primers for three different infectious diseases: ZIKV, DENV, and CHIKV may be utilized. Well-proven rRT-PCR reagents including each primer for ZIKV, DENV, and CHIKV may be purchased from Thermo Fisher Scientific (cat #: A31746, TaqMan® Zika Virus Triplex Kit (ZIKV/DENV/CHIKV)). The reagents are pre-lyophilized to be stable in room temperature and are ready to be rehydrated for rRT-PCR. A 200-µL real-time PCR tube may be used as a cartridge in the beginning phase of the project, and an SLA 3D printer may be used in the later phase to fabricate an optimal cartridge.

According to various embodiments, a well-designed user interface may be important because the device is expected to be used by clinicians and medical staffs. The user interface may be designed to allow the user to change variables associated with real-time PCR cycles, such as thermocycling temperatures, durations, and fluorescence reading. In the control assembly (FIG. 17), an LCD screen may display the user's selections that can be changed by navigation buttons. Once the real-time PCR cycle is executed, the LCD may be used to display the temperature versus time to indicate the progress of the assay and show fluorescence readings after each cycle. The reading may be in relative fluorescence units (RFU), which is based on the processing of the data in the MCU. The user interface may be developed with a strong focus on an easy-to-use and intuitive interface for users. Also, the device may be integrated with telemetry modules, such as a Bluetooth module, to enable wireless communication for data transmission and advanced maintenance. The device may be able to remotely pair with a nearby smartphone using a Bluetooth module where advanced functions can be executed.

Upon reading the present disclosure a person having ordinary skill in the art will be readily equipped to quantify the efficacy of the integrated syringe and real-time PCR device. To test the efficacy of the workflow from drawing blood to real-time PCR detection, the SLA 3D-printed integrated syringe may be tested in conjunction with the real-time PCR device. For this test, whole blood spiked with ZIKV and DENV may be drawn into the integrated syringe for RNA purification. Spiked samples will have known concentrations of RNA in the range of $10^2$-$10^7$ per mL that will exhibit different Ct values during real-time PCR cycles. The syringe and a cartridge may be inserted into the side of the real-time PCR device (FIGS. 1 and 2). The user may press the plunger which causes the elution of RNA from the silica membrane 34. The eluted RNA will be ejected through the inlet of the syringe and transferred into the cartridge causing a rehydration of the lyophilized reagents. By pressing a start button on the front panel of the real-time PCR device, the cartridge will undergo thermocycling for the nucleic acid amplification. The fluorescence measurement from the real-time PCR device may be compared to that of a benchtop-purified RNA. The measured Ct values may be used to calculate the cDNA amplification factor per cycle which is theoretically ~2 per cycle. Thus, ideally, the Ct values should be 3.32 cycles apart between 10 times dilutions. Using this standard, the real-time PCR device may be optimized to match the performance of the high-quality commercial real-time PCR device (Thermo 7900HT Fast Real-Time PCR System).

For the validation of the real-time PCR device, a person having ordinary skill in the art will anticipate the amplification factor to be 2 per cycle. Typically, non-ideal amplification factors are due to imperfect temperature control that fails to denature or extend all the DNA within each cycle. Therefore, the temperature of real-time PCR tubes may be carefully calibrated with a close-loop control using MCU.

Various embodiments may include a check valve that allows the flow of a fluid through the valve in only one direction. In the syringe the check valve may be used for several purposes. For example, when blood is wished to be drawn from the needle into the syringe, it must first be pulled through a check valve, in this way, blood may flow into the syringe, but should the operator push the plunger in, blood or any other mixture of reagents is prevented from exiting the syringe through the needle. It is also used for several of the syringe's reservoirs. These reservoirs will be preloaded with appropriate reagents (such as lysis buffer, washing buffer, or elusion buffer) and must be able to be removed from their reservoirs into the internal structures of the syringe without any risk of leaking out of the syringe into the environment. A check valve between these reservoirs and the air allows for the reservoirs to be filled, but not for the contents of the reservoirs to leak out of the syringe. The valve consists of two housings that serve as the inlet and outlet ports. The two housings are assembled together using screws and are sealed with the Sealing O-ring inserted into a groove in the Inlet Housing. The functional part of the valve is known as a poppet. The poppet may be a piece of plastic which holds a small O-ring which provides the sealing action. A spring or other suitable means may force the poppet to be pushed towards the inlet housing, which may have a tapered shape. This causes the O-ring to seal against the housing, preventing liquid from travelling towards the inlet. However, if the pressure is higher on the inlet side than the outlet side, then the poppet is permitted to move away from the inlet housing, allowing for liquid to flow into the chamber surrounding the poppet assembly.

Figure 19A:
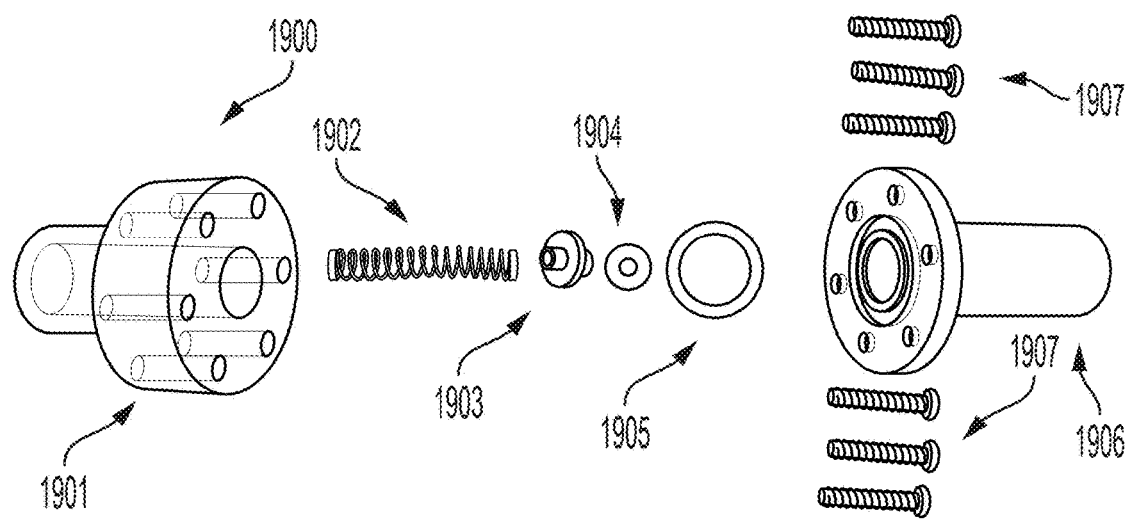
FIG. 19A is an example according to various embodiments illustrating photographs of components of an valve organized as an exploded view of the valve.
Figure 19B:
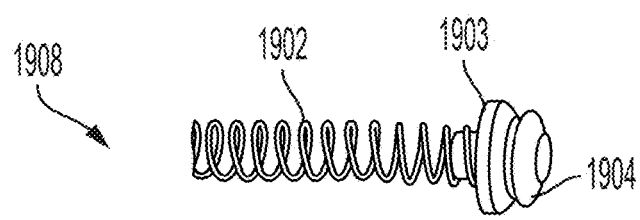
FIG. 19B is an example according to various embodiments illustrating a photograph of a poppet used in the valve shown in FIG. 19A.
Figure 19C:
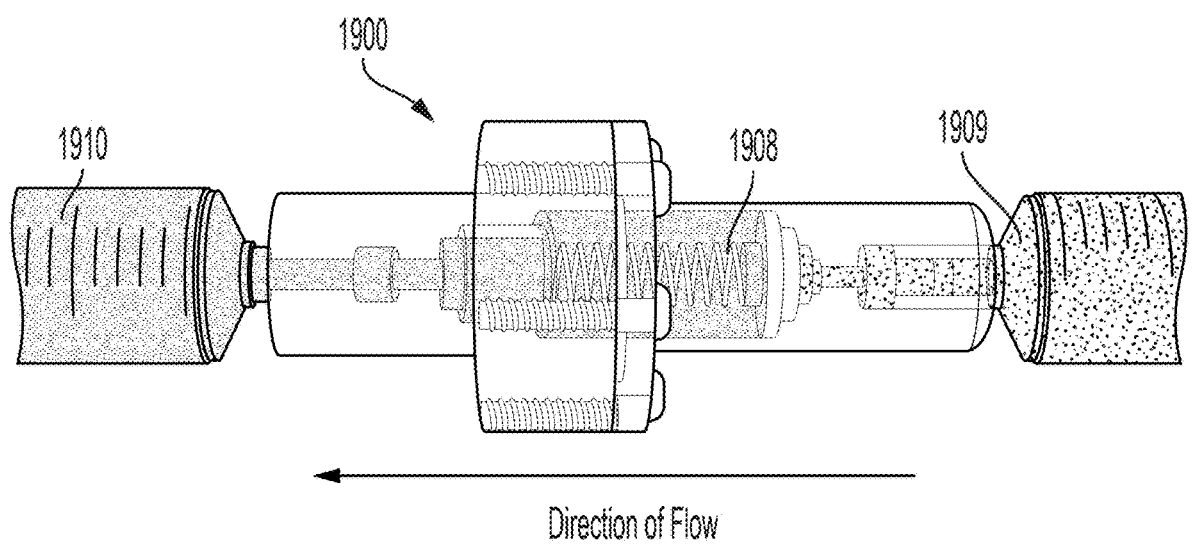
FIG. 19C is an example according to various embodiments illustrating a photograph of an assembled valve, components of which are shown in FIG. 19A.

FIG. 19A is an example according to various embodiments illustrating photographs of components of a check valve 1900 organized as an exploded view of the valve. The check valve 1900 includes an outlet housing 1901 and an inlet housing 1906, which may be secured together by any suitable means, including, for example, via a plurality of screws 1907. As illustrated in FIGS. 19A and 19B, a poppet 1908 may be housed within the check valve 1900. The poppet assembly 1908 may include a spring, a poppet 1903, and gasket or an o-ring 1904. The check valve 1900 may further include a second gasket or a second o-ring 1905 sandwiched between the outlet housing 1901 and the inlet housing 1906. FIG. 19C is an example according to various embodiments illustrating a photograph of an assembled valve 1900, components of which are shown in FIG. 19A. The check valve 1900 allows a first fluid 1909 to enter through the inlet 1906 but restricts flow of a second fluid 1910 to flow through the inlet 1906.

FIGS. 20A-20G are examples according to various embodiments illustrating the rotary valve mechanism 2000 enables the syringe 2007 to perform multiple actions in one device. FIG. 20A is an example according to various embodiments illustrating a photograph of a barrel portion 2001 of a rotary valve mechanism 200 that may form the outer surface or shell of a syringe. FIG. 20B is an example according to various embodiments illustrating a photograph of a central valve body 2002. The rotary valve mechanism may operate by rotation of the central valve body 2002 within a barrel 2001.

Various reservoirs 2003 and chambers 2004 may be housed in the barrel portion 2001 of the rotary valve mechanism 2000, which have fluidic channels 2005 that connect these reservoirs 2003 and chambers 2004 to the inside of the barrel 2001. The central valve body 2002 is inserted into the barrel 2001, with rubber O-rings 2008 installed around the fluidic ports 2005 exposed on the inside of the barrel 2001. The O-rings 2008 provide a means of sealing these chambers against leakage when not currently selected by the inner valve body 2002. The barrel 2001 may have grooves 2009 around the exposes ports 2005 that firmly hold the O-rings 2008 in place when the inner valve body 2002 is inserted. Within the valve body 2002, there are also fluidic channels 2010, such as the one housing a silica filter 2011, which allow transport of liquids to and from the ports on the side of the valve body 2002. When rotated, these ports are placed in line with the fluidic ports 2005 on the barrel 2001 of the syringe 2007 forming a complete fluidic channel. The inner valve body can be rotated to multiple positions to facilitate several fluidic circuits corresponding to each step of the sample preparation process. Precise rotation from a first position as shown in FIG. 20E to a second position as shown in FIG. 20F may be facilitated by aligning a first position indicator 2012 on the inner valve body 2002 with one of a plurality of position indicators 2013 on the barrel 2001. For example, FIG. 20E is an example according to various embodiments illustrating a photograph of the assembled syringe as shown in FIG. 20C in a first configuration, selecting one of the positions filled with blue liquid. Similarly, FIG. 20F is an example according to various embodiments illustrating a photograph of the assembled syringe as shown in FIG. 20C in a second configuration, selecting one of the positions filled with red liquid.

FIGS. 21A-21H are examples according to various embodiments illustrating the cylindrical cam mechanism 2100 that may all the rotary valve to be positioned correctly for each of the steps of the sample preparation process. The cam works by having an outer shell 2102 which contains a groove 2103 running down the length of the inside wall. Inserted into the cylinder is the plunger 2101 of the syringe, and the syringe body. The plunger is pulled out by the user of the syringe. The plunger is similar to a traditional syringe, with the addition of pins 2104 that extend outwards that are inserted into the groove in the syringe body and extend into the cam groove in the outer cylinder. The outer cylinder groove's geometry is designed so that at different positions along the height of the cylinder, the groove is at different angular positions. Since the pins on the plunger ride within this groove, the plunger is rotated according to the groove's geometry as it is pulled out. The plunger of the syringe is to be coupled to the rotary valve so that when it is pulled, each step of the sample preparation process is completed one after another with a single pull of the plunger. FIG. 21A is an example according to various embodiments illustrating a side view photograph of a cylindrical cam in a first position, the cylindrical cam comprising a plunger and a syringe body, the plunger having pins that engage a groove in the syringe body. FIG. 21B is an example according to various embodiments illustrating a top view photograph of the cylindrical cam as shown in FIG. 21A in the first position. FIG. 21C is an example according to various embodiments illustrating a side view photograph of the cylindrical cam as shown in FIG. 21A in a second position. FIG. 21D is an example according to various embodiments illustrating a top view photograph of the cylindrical cam as shown in FIG. 21C in the second position. FIG. 21E is an example according to various embodiments illustrating a side view photograph of the cylindrical cam as shown in FIG. 21A in a third position. FIG. 21F is an example according to various embodiments illustrating a top view photograph of the cylindrical cam as shown in FIG. 21E in the third position. FIG. 21G is an example according to various embodiments illustrating a side view photograph of the cylindrical cam as shown in FIG. 21A in a fourth position. FIG. 21H is an example according to various embodiments illustrating a top view photograph of the cylindrical cam as shown in FIG. 21G in the fourth position.

Figure 22A:
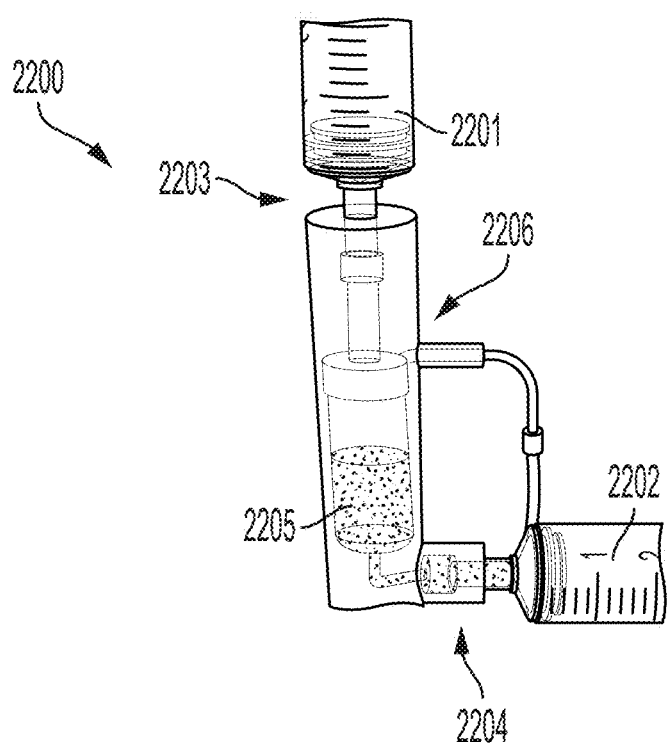
FIG. 22A is an example according to various embodiments illustrating a photograph of the test assembly performing a mixing operation in a first stage.
Figure 22B:
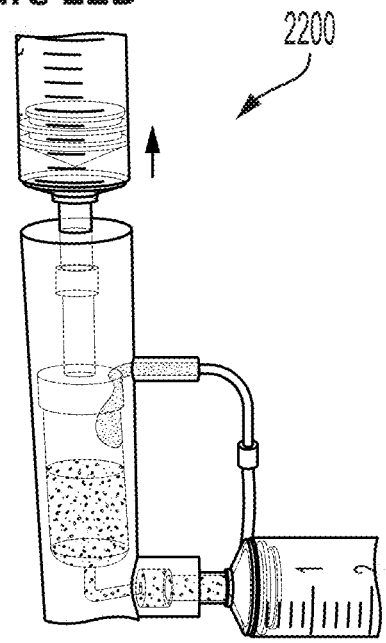
FIG. 22B is an example according to various embodiments illustrating a photograph of the test assembly shown in FIG. 22A performing a mixing operation in a second stage.
Figure 22C:
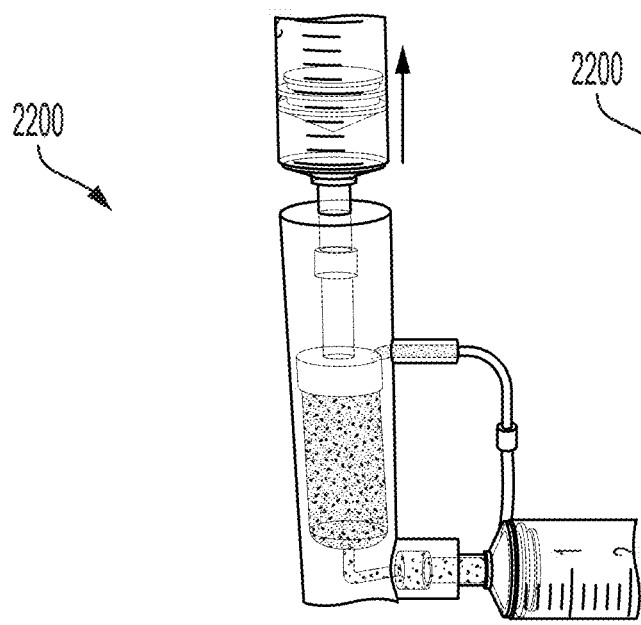
FIG. 22C is an example according to various embodiments illustrating a photograph of the test assembly shown in FIG. 22A performing a mixing operation in a third stage.
Figure 22D:
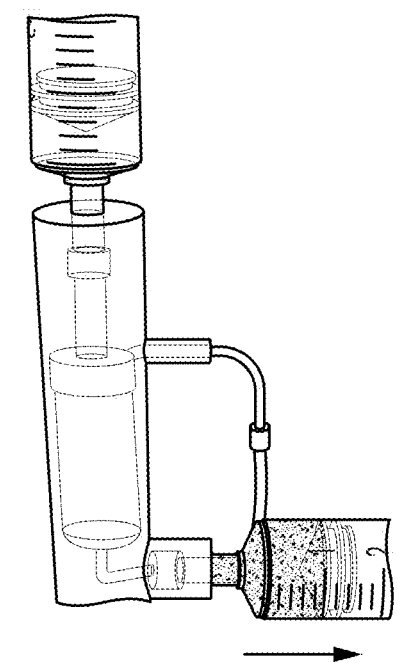
FIG. 22D is an example according to various embodiments illustrating a photograph of the test assembly shown in FIG. 22A performing a mixing operation in a fourth stage.

FIGS. 22A-22D are examples according to various embodiments illustrating the mixing reservoir is a special type of reservoir designed to allow the mixing of two reagents within it using only the vacuum produced by the syringe to perform the mixing. According to various embodiments, each of the ports may be connected to the rotary valve, allowing for a single pull to complete all 4 steps with one pull of a single plunger. FIGS. 22A-22D provide a demonstration of a test assembly 2200 in which a first syringe 2201 and a second syringe 2202 are used to apply vacuum to a vacuum port 2203 and a drain port 2204, and a simple reservoir 2205 and piece of tubing connected to an inlet port 2206 is used to simulate the needle. The reservoir 2205 has 3 ports: the vacuum port 2203, the inlet port 2206, and the drain port 2204. FIG. 22A is an example according to various embodiments illustrating a photograph of the test assembly 2202 performing a mixing operation in a first stage. FIG. 22B is an example according to various embodiments illustrating a photograph of the test assembly 2202 shown in FIG. 22A performing a mixing operation in a second stage. FIG. 22C is an example according to various embodiments illustrating a photograph of the test assembly 2202 shown in FIG. 22A performing a mixing operation in a third stage. FIG. 22D is an example according to various embodiments illustrating a photograph of the test assembly 2202 shown in FIG. 22A performing a mixing operation in a fourth stage.

A mixing operation may be performed using the test assembly 2200. In the first stage illustrated in FIG. 22A, the reservoir 2205 may be preloaded with reagent 1 (Blue). In the second stage illustrated in FIG. 22B, a vacuum may be pulled on the vacuum port 2203 while reagent 2 (Red) is pulled into the reservoir 2205 through inlet port due 2204 to vacuum and falls into reservoir by gravity. In the third stage illustrated in FIG. 22C, reagent 1 and 2 are mixed together with additional vacuum added. Finally, in the fourth stage illustrated in FIG. 22D, the mixture of reagent 1 and 2 is pulled out through the drain port 2204.

Computational Hardware Overview

Figure 23:
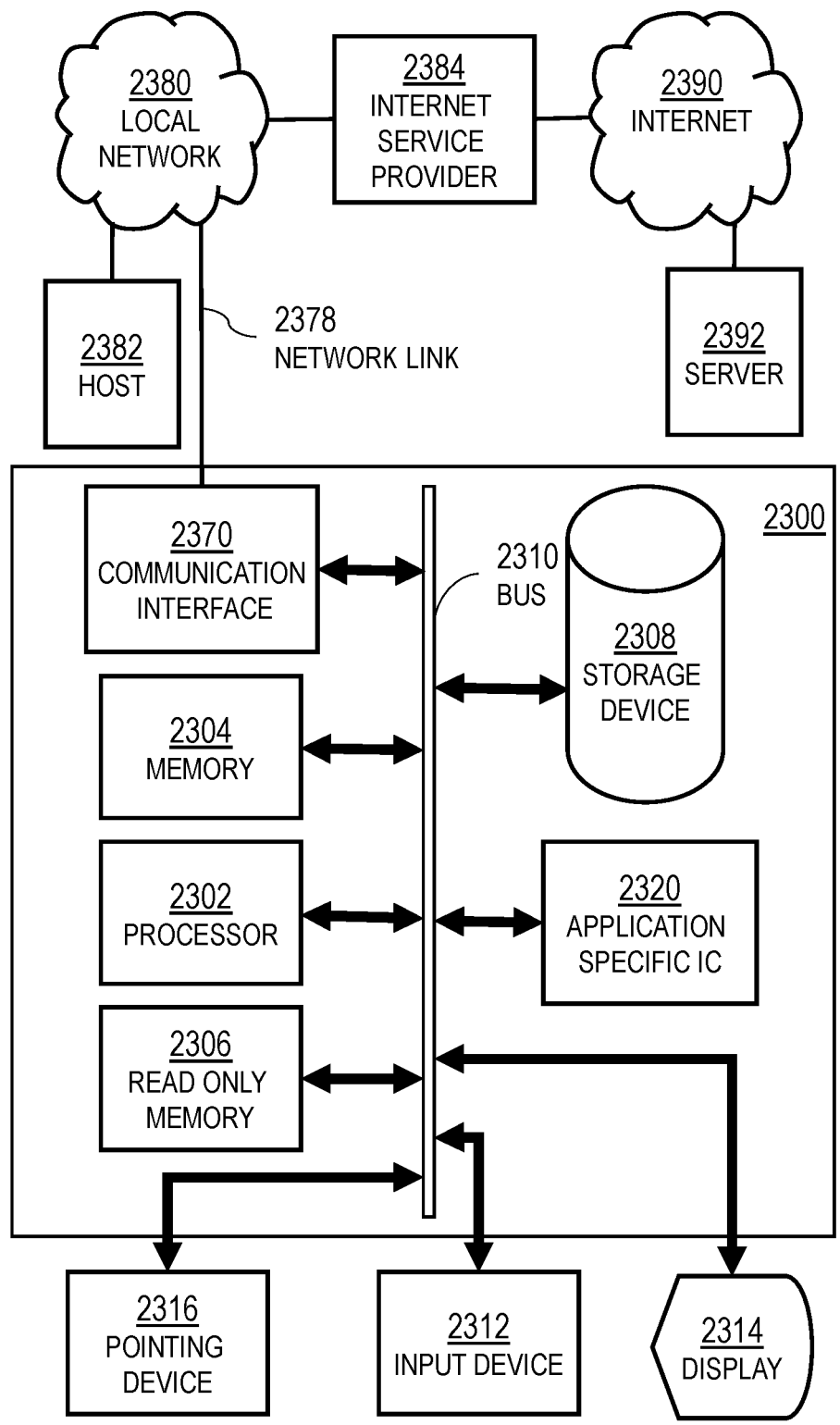
FIG. 23 is a block diagram that illustrates a computer system upon which an embodiment of the invention may be implemented.

FIG. 23 is a block diagram that illustrates a computer system 2300 upon which an embodiment of the invention may be implemented. Computer system 2300 includes a communication mechanism such as a bus 2310 for passing information between other internal and external components of the computer system 2300. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 2300, or a portion thereof, constitutes a means for performing one or more steps of one or more methods described herein.

A sequence of binary digits constitutes digital data that is used to represent a number or code for a character. A bus 2310 includes many parallel conductors of information so that information is transferred quickly among devices coupled to the bus 2310. One or more processors 2302 for processing information are coupled with the bus 2310. A processor 2302 performs a set of operations on information. The set of operations include bringing information in from the bus 2310 and placing information on the bus 2310. The set of operations also typically include comparing two or more units of information, shifting positions of units of information, and combining two or more units of information, such as by addition or multiplication. A sequence of operations to be executed by the processor 2302 constitutes computer instructions.

Computer system 2300 also includes a memory 2304 coupled to bus 2310. The memory 2304, such as a random access memory (RAM) or other dynamic storage device, stores information including computer instructions. Dynamic memory allows information stored therein to be changed by the computer system 2300. RAM allows a unit of information stored at a location called a memory address to be stored and retrieved independently of information at neighboring addresses. The memory 2304 is also used by the processor 2302 to store temporary values during execution of computer instructions. The computer system 2300 also includes a read only memory (ROM) 2306 or other static storage device coupled to the bus 2310 for storing static information, including instructions, that is not changed by the computer system 2300. Also coupled to bus 2310 is a non-volatile (persistent) storage device 2308, such as a magnetic disk or optical disk, for storing information, including instructions, that persists even when the computer system 2300 is turned off or otherwise loses power.

Information, including instructions, is provided to the bus 2310 for use by the processor from an external input device 2312, such as a keyboard containing alphanumeric keys operated by a human user, or a sensor. A sensor detects conditions in its vicinity and transforms those detections into signals compatible with the signals used to represent information in computer system 2300. Other external devices coupled to bus 2310, used primarily for interacting with humans, include a display device 2314, such as a cathode ray tube (CRT) or a liquid crystal display (LCD), for presenting images, and a pointing device 2316, such as a mouse or a trackball or cursor direction keys, for controlling a position of a small cursor image presented on the display 2314 and issuing commands associated with graphical elements presented on the display 2314.

In the illustrated embodiment, special purpose hardware, such as an application specific integrated circuit (IC) 2320, is coupled to bus 2310. The special purpose hardware is configured to perform operations not performed by processor 2302 quickly enough for special purposes. Examples of application specific ICs include graphics accelerator cards for generating images for display 2314, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 2300 also includes one or more instances of a communications interface 2370 coupled to bus 2310. Communication interface 2370 provides a two-way communication coupling to a variety of external devices that operate with their own processors, such as printers, scanners and external disks. In general the coupling is with a network link 2378 that is connected to a local network 2380 to which a variety of external devices with their own processors are connected. For example, communication interface 2370 may be a parallel port or a serial port or a universal serial bus (USB) port on a personal computer. In some embodiments, communications interface 2370 is an integrated services digital network (ISDN) card or a digital subscriber line (DSL) card or a telephone modem that provides an information communication connection to a corresponding type of telephone line. In some embodiments, a communication interface 2370 is a cable modem that converts signals on bus 2310 into signals for a communication connection over a coaxial cable or into optical signals for a communication connection over a fiber optic cable. As another example, communications interface 2370 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 2370 sends and receives electrical, acoustic or electromagnetic signals, including infrared and optical signals, that carry information streams, such as digital data.

The term computer-readable medium is used herein to refer to any medium that participates in providing information to processor 2302, including instructions for execution. Such a medium may take many forms, including, but not limited to, non-volatile media, volatile media and transmission media. Non-volatile media include, for example, optical or magnetic disks, such as storage device 2308. Volatile media include, for example, dynamic memory 2304. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 2302, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 2302, except for carrier waves and other signals.

Logic encoded in one or more tangible media includes one or both of processor instructions on a computer-readable storage media and special purpose hardware, such as ASIC 2320.

Network link 2378 typically provides information communication through one or more networks to other devices that use or process the information. For example, network link 2378 may provide a connection through local network 2380 to a host computer 2382 or to equipment 2384 operated by an Internet Service Provider (ISP). ISP equipment 2384 in turn provides data communication services through the public, world-wide packet-switching communication network of networks now commonly referred to as the Internet 2390. A computer called a server 2392 connected to the Internet provides a service in response to information received over the Internet. For example, server 2392 provides information representing video data for presentation at display 2314.

The invention is related to the use of computer system 2300 for implementing the techniques described herein. According to one embodiment of the invention, those techniques are performed by computer system 2300 in response to processor 2302 executing one or more sequences of one or more instructions contained in memory 2304. Such instructions, also called software and program code, may be read into memory 2304 from another computer-readable medium such as storage device 2308. Execution of the sequences of instructions contained in memory 2304 causes processor 2302 to perform the method steps described herein. In alternative embodiments, hardware, such as application specific integrated circuit 2320, may be used in place of or in combination with software to implement the invention. Thus, embodiments of the invention are not limited to any specific combination of hardware and software.

The signals transmitted over network link 2378 and other networks through communications interface 2370, carry information to and from computer system 2300. Computer system 2300 can send and receive information, including program code, through the networks 2380, 2390 among others, through network link 2378 and communications interface 2370. In an example using the Internet 2390, a server 2392 transmits program code for a particular application, requested by a message sent from computer 2300, through Internet 2390, ISP equipment 2384, local network 2380 and communications interface 2370. The received code may be executed by processor 2302 as it is received, or may be stored in storage device 2308 or other non-volatile storage for later execution, or both. In this manner, computer system 2300 may obtain application program code in the form of a signal on a carrier wave.

Various forms of computer readable media may be involved in carrying one or more sequence of instructions or data or both to processor 2302 for execution. For example, instructions and data may initially be carried on a magnetic disk of a remote computer such as host 2382. The remote computer loads the instructions and data into its dynamic memory and sends the instructions and data over a telephone line using a modem. A modem local to the computer system 2300 receives the instructions and data on a telephone line and uses an infra-red transmitter to convert the instructions and data to a signal on an infra-red a carrier wave serving as the network link 2378. An infrared detector serving as communications interface 2370 receives the instructions and data carried in the infrared signal and places information representing the instructions and data onto bus 2310. Bus 2310 carries the information to memory 2304 from which processor 2302 retrieves and executes the instructions using some of the data sent with the instructions. The instructions and data received in memory 2304 may optionally be stored on storage device 2308, either before or after execution by the processor 2302.

Figure 24:
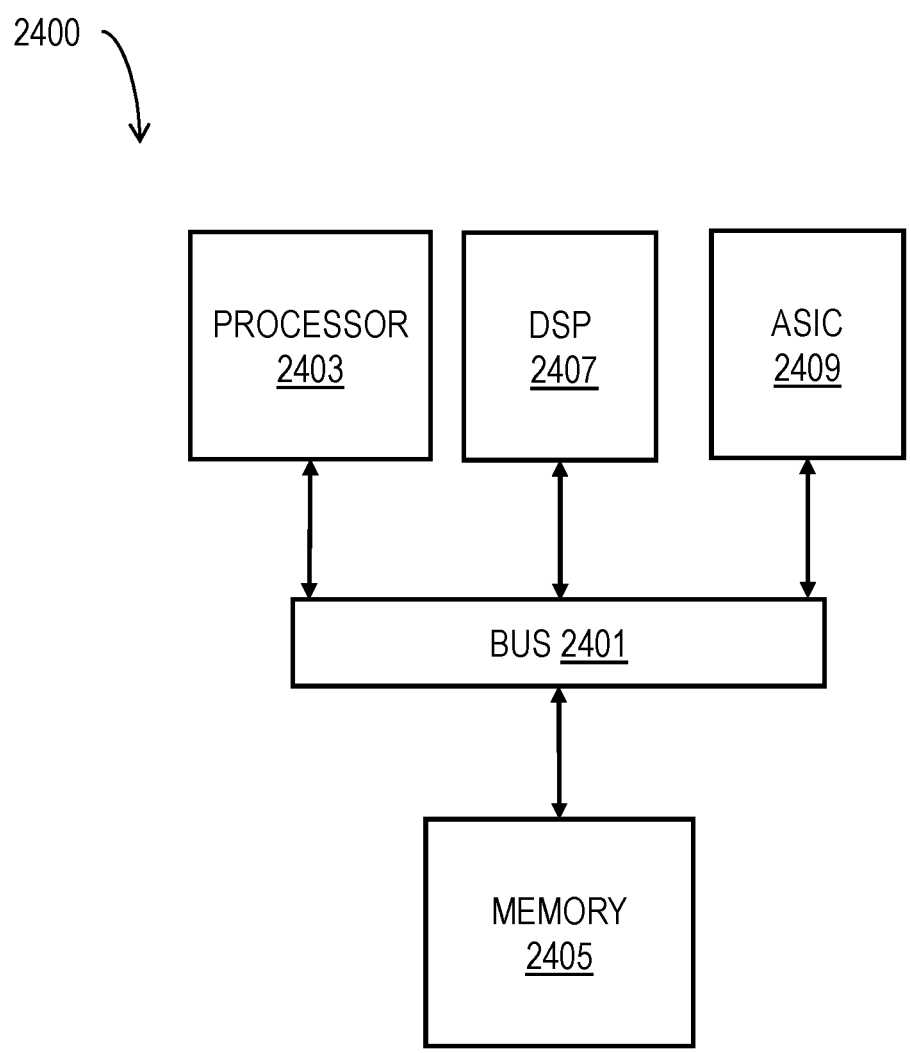
FIG. 24 illustrates a chip set upon which an embodiment of the invention may be implement.

FIG. 24 illustrates a chip set 2400 upon which an embodiment of the invention may be implemented. Chip set 2400 is programmed to perform one or more steps of a method described herein and includes, for instance, the processor and memory components described with respect to FIG. 23 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 2400, or a portion thereof, constitutes a means for performing one or more steps of a method described herein.

In one embodiment, the chip set 2400 includes a communication mechanism such as a bus 2401 for passing information among the components of the chip set 2400. A processor 2403 has connectivity to the bus 2401 to execute instructions and process information stored in, for example, a memory 2405. The processor 2403 may include one or more processing cores with each core configured to perform independently. A multi-core processor enables multiprocessing within a single physical package. Examples of a multi-core processor include two, four, eight, or greater numbers of processing cores. Alternatively or in addition, the processor 2403 may include one or more microprocessors configured in tandem via the bus 2401 to enable independent execution of instructions, pipelining, and multithreading. The processor 2403 may also be accompanied with one or more specialized components to perform certain processing functions and tasks such as one or more digital signal processors (DSP) 2407, or one or more application-specific integrated circuits (ASIC) 2409. A DSP 2407 typically is configured to process real-world signals (e.g., sound) in real time independently of the processor 2403. Similarly, an ASIC 2409 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 2403 and accompanying components have connectivity to the memory 2405 via the bus 2401. The memory 2405 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 2405 also stores the data associated with or generated by the execution of one or more steps of the methods described herein.

What is claimed is:

1. A syringe for separating nucleic acids from a blood sample, the syringe comprising:
    a shell defining a central aperture extending through a longitudinal axis of the syringe, the shell comprising
        an inlet,
        a follower extending into the central aperture,
        a first chamber defined within a thickness of the shell,
        a first chamber inlet fluidically connecting the first chamber to the central aperture of the shell, and
        a first chamber outlet fluidically connecting the first chamber to the central aperture of the shell,
    a plunger disposed within the central aperture of the shell, the plunger comprising
        a profiled portion disposable within the central aperture to engage the follower of the shell to cause a rotational displacement about the longitudinal axis when the plunger is displaced along the longitudinal axis;
    a core rotatably disposed within the central aperture, the core comprising
        a membrane disposed within the core,
        a first channel disposable to form a fluidic connection between the inlet of the shell and the first chamber inlet, and
        a second channel disposable to form a fluidic connection between the first chamber outlet and the membrane.

2. The syringe according to claim 1, further comprising a needle fluidically connectable to the inlet of the shell.

3. The syringe according to claim 1, wherein the first chamber is at least partially filled with a lysis buffer.

4. The syringe according to claim 1, wherein the shell further comprises
    a second chamber defined within a thickness of the shell,
    a second chamber inlet fluidically connecting the second chamber to the central aperture of the shell, and
    a second chamber outlet fluidically connecting the second chamber to the central aperture of the shell; and
wherein the core further comprises
    a first expandable cavity;
    a third channel disposable to form a fluidic connection between the membrane and the second chamber inlet, and
    a fourth channel disposable to form a fluidic connection between the second chamber outlet and the first expandable cavity; and
wherein the plunger further comprises a first prong disposable within the first expandable cavity.

5. The syringe according to claim 4, wherein the second chamber is at least partially filled with a washing buffer.

6. The syringe according to claim 4, wherein the shell further comprises
    a third chamber defined within a thickness of the shell,
    a third chamber inlet fluidically connecting the third chamber to the central aperture of the shell,
    a third chamber outlet fluidically connecting the third chamber to the central aperture of the shell, and
    optionally an outlet; and
wherein the core further comprises
    a second expandable cavity;
    a fifth channel disposable to form a fluidic connection between the second expandable cavity and the third chamber inlet, and
    optionally a fifth channel disposable to form a fluidic connection between the third chamber outlet and the outlet of the shell; and
wherein the plunger further comprises a second prong disposable within the second expandable cavity.

7. The syringe according to claim 1, further comprising a check valve disposed between the inlet and the first chamber, the check valve being oriented to limit backflow from the first chamber toward the inlet.

8. A method for separating nucleic acids from a blood sample, the method comprising drawing the blood sample from a patient using the syringe according to claim 1.

9. A system comprising a syringe and a portable PCR device adapted to receive nucleic acids from the syringe, the syringe comprising
    a shell defining a central aperture extending through a longitudinal axis of the syringe, the shell comprising
        an inlet,
        a follower extending into the central aperture,
        a first chamber defined within a thickness of the shell,
        a first chamber inlet fluidically connecting the first chamber to the central aperture of the shell, and
        a first chamber outlet fluidically connecting the first chamber to the central aperture of the shell,
    a plunger disposed within the central aperture of the shell, the plunger comprising
        a profiled portion disposable within the central aperture to engage the follower of the shell to cause a rotational displacement about the longitudinal axis when the plunger is displaced along the longitudinal axis;
    a core rotatably disposed within the central aperture, the core comprising
        a membrane disposed within the core,
        a first channel disposable to form a fluidic connection between the inlet of the shell and the first chamber inlet, and
        a second channel disposable to form a fluidic connection between the first chamber outlet and the membrane.

10. The system according to claim 9, further comprising a needle fluidically connectable to the inlet of the shell.

11. A method for detecting an agent in a sample, using the system according to claim 9, the method comprising:
    separating nucleic acids from a blood sample by drawing the blood sample through the syringe; and
    testing the nucleic acids in a portable PCR device to detect the agent.

* * * * *